(12) United States Patent
Howell et al.

(10) Patent No.: US 10,456,497 B2
(45) Date of Patent: Oct. 29, 2019

(54) PROTECTIVE DRESSING FOR SKIN-PLACED MEDICAL DEVICE

(71) Applicant: C. R. Bard, Inc., Murray Hill, NJ (US)

(72) Inventors: Glade H. Howell, Draper, UT (US); Kelly J. Christian, Draper, UT (US); Matthew W. Bown, West Bountiful, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 849 days.

(21) Appl. No.: 14/850,825

(22) Filed: Sep. 10, 2015

(65) Prior Publication Data

US 2016/0067106 A1 Mar. 10, 2016

Related U.S. Application Data

(60) Provisional application No. 62/048,747, filed on Sep. 10, 2014.

(51) Int. Cl.
*A61F 13/00* (2006.01)
*A61M 5/32* (2006.01)
(Continued)

(52) U.S. Cl.
CPC .......... *A61L 15/26* (2013.01); *A61F 13/0203* (2013.01); *A61F 15/008* (2013.01);
(Continued)

(58) Field of Classification Search
USPC .................................. 604/180; 128/888, 889
See application file for complete search history.

(56) References Cited

U.S. PATENT DOCUMENTS 697,637 A * 4/1902 Lee .................. A61F 15/008
128/888
RE24,906 E 12/1960 Ulrich
(Continued)

FOREIGN PATENT DOCUMENTS

EP 5193 A1 11/1979
EP 368541 A1 5/1990
(Continued)

OTHER PUBLICATIONS

US 7,390,501 B2, 06/2008, Hart et al. (withdrawn)
(Continued)

*Primary Examiner* — Kim M Lewis
(74) *Attorney, Agent, or Firm* — Rutan & Tucker, LLP

(57) ABSTRACT

A dressing for use in protectively covering and isolating a medical device placed on and/or through the skin surface of a patient is disclosed. Examples of such devices include infusion needles for accessing subcutaneously implanted access ports, catheters of various types and purposes, insulin infusion needles, etc. In one embodiment, a dressing for covering a medical device on a skin surface of a patient is disclosed and comprises a dressing portion that is configured to rest against a skin surface of a patient, with the dressing portion defining a hole, and a polymeric cover film that is at least indirectly attached to the dressing portion. The cover film includes a pliable domed portion aligned with the hole of the dressing portion. The pliable domed portion defines a cavity that is configured to receive therein the medical device when the dressing is placed on the skin of the patient.

25 Claims, 16 Drawing Sheets

(51) Int. Cl.
   *A61L 15/26*    (2006.01)
   *A61M 25/02*   (2006.01)
   *A61F 15/00*    (2006.01)
   *A61F 13/02*    (2006.01)

(52) U.S. Cl.
   CPC ... *A61M 25/02* (2013.01); *A61F 2013/00412* (2013.01); *A61F 2013/00829* (2013.01)

(56) References Cited

U.S. PATENT DOCUMENTS

| | | |
|---|---|---|
| 3,389,827 A | 6/1968 | Abere et al. |
| 3,645,835 A | 2/1972 | Hodgson |
| 3,683,911 A | 8/1972 | McCormick |
| 3,782,377 A | 1/1974 | Rychlik |
| 3,824,998 A | 7/1974 | Snyder |
| 3,900,026 A | 8/1975 | Wagner |
| 4,112,213 A | 9/1978 | Waldman |
| 4,181,127 A | 1/1980 | Linsky et al. |
| 4,231,369 A | 11/1980 | Sorensen et al. |
| 4,275,721 A | 6/1981 | Olson |
| 4,310,509 A | 1/1982 | Berglund et al. |
| 4,323,557 A | 4/1982 | Rosso et al. |
| 4,366,814 A | 1/1983 | Riedel |
| 4,372,303 A | 2/1983 | Grossmann et al. |
| 4,373,519 A | 2/1983 | Errede et al. |
| 4,472,480 A | 9/1984 | Olson |
| 4,477,325 A | 10/1984 | Osburn |
| 4,499,896 A | 2/1985 | Heinecke |
| 4,519,793 A | 5/1985 | Galindo |
| 4,524,087 A | 6/1985 | Engel |
| 4,534,762 A | 8/1985 | Heyer |
| 4,551,490 A | 11/1985 | Doyle et al. |
| 4,565,663 A | 1/1986 | Errede et al. |
| 4,598,004 A | 7/1986 | Heinecke |
| 4,600,001 A | 7/1986 | Gilman |
| 4,614,183 A | 9/1986 | McCracken et al. |
| 4,619,253 A | 10/1986 | Anhauser et al. |
| 4,633,863 A | 1/1987 | Filips et al. |
| 4,667,666 A | 5/1987 | Fryslie |
| 4,669,458 A | 6/1987 | Abraham et al. |
| 4,675,006 A | 6/1987 | Hrushesky |
| 4,678,462 A | 7/1987 | Vaillancourt |
| 4,693,776 A | 9/1987 | Krampe et al. |
| 4,706,662 A | 11/1987 | Thompson |
| 4,728,323 A | 3/1988 | Matson |
| 4,737,410 A | 4/1988 | Kantner |
| 4,738,257 A | 4/1988 | Meyer et al. |
| 4,769,028 A | 9/1988 | Hoffmann et al. |
| 4,773,408 A | 9/1988 | Cilento et al. |
| 4,830,914 A | 5/1989 | Vaillancourt |
| 4,867,150 A | 9/1989 | Gilbert |
| 4,867,742 A | 9/1989 | Calderon |
| 4,867,748 A | 9/1989 | Samuelsen |
| 4,898,587 A * | 2/1990 | Mera ............ A61M 25/02 128/DIG. 26 |
| 4,901,714 A | 2/1990 | Jensen |
| 4,909,244 A | 3/1990 | Quarfoot et al. |
| 4,917,112 A | 4/1990 | Kalt |
| 4,917,928 A | 4/1990 | Heinecke |
| 4,917,929 A | 4/1990 | Heinecke |
| 4,919,654 A | 4/1990 | Kalt |
| 4,931,282 A | 6/1990 | Asmus et al. |
| 4,944,040 A | 7/1990 | Riedel et al. |
| 4,948,575 A | 8/1990 | Cole et al. |
| 4,952,618 A | 8/1990 | Olsen |
| RE33,353 E | 9/1990 | Heinecke |
| 4,956,350 A | 9/1990 | Mosbey |
| 4,977,892 A | 12/1990 | Ewall |
| 4,988,341 A | 1/1991 | Columbus et al. |
| 5,000,172 A | 3/1991 | Ward |
| 5,009,224 A | 4/1991 | Cole |
| 5,017,625 A | 5/1991 | Ansell |
| 5,059,424 A | 10/1991 | Cartmell et al. |
| 5,074,847 A | 12/1991 | Greenwell et al. |
| 5,088,483 A | 2/1992 | Heinecke |
| 5,106,629 A | 4/1992 | Cartmell et al. |
| 5,113,860 A | 5/1992 | McQuinn |
| 5,133,821 A | 7/1992 | Jensen |
| 5,151,314 A | 9/1992 | Brown |
| 5,153,040 A | 10/1992 | Faasse, Jr. |
| 5,156,601 A | 10/1992 | Lorenz et al. |
| 5,160,315 A | 11/1992 | Heinecke et al. |
| 5,197,945 A | 3/1993 | Cole et al. |
| 5,225,473 A | 7/1993 | Duan |
| 5,236,421 A | 8/1993 | Becher |
| 5,244,677 A | 9/1993 | Kreckel et al. |
| 5,250,043 A | 10/1993 | Castellana et al. |
| 5,266,371 A | 11/1993 | Sugii et al. |
| 5,270,358 A | 12/1993 | Asmus |
| 5,276,079 A | 1/1994 | Duan et al. |
| 5,282,791 A | 2/1994 | Lipton et al. |
| 5,308,887 A | 5/1994 | Ko et al. |
| 5,338,490 A | 8/1994 | Dietz et al. |
| 5,340,363 A | 8/1994 | Fabo |
| 5,344,415 A | 9/1994 | DeBusk et al. |
| 5,356,632 A | 10/1994 | Gross et al. |
| 5,384,174 A | 1/1995 | Ward et al. |
| 5,386,835 A | 2/1995 | Elphick et al. |
| 5,389,376 A | 2/1995 | Duan et al. |
| 5,409,472 A | 4/1995 | Rawlings et al. |
| 5,409,966 A | 4/1995 | Duan et al. |
| 5,413,567 A | 5/1995 | Barth et al. |
| 5,415,642 A | 5/1995 | Shepherd |
| 5,423,737 A | 6/1995 | Cartmell et al. |
| 5,437,622 A | 8/1995 | Carion |
| 5,438,988 A | 8/1995 | Duan et al. |
| 5,447,492 A | 9/1995 | Cartmell et al. |
| 5,509,915 A | 4/1996 | Hanson et al. |
| 5,512,041 A | 4/1996 | Bogart |
| 5,520,629 A | 5/1996 | Heinecke et al. |
| 5,531,855 A | 7/1996 | Heinecke et al. |
| 5,536,544 A | 7/1996 | Liegeois |
| 5,540,922 A | 7/1996 | Fabo |
| 5,556,375 A | 9/1996 | Ewall |
| 5,593,395 A | 1/1997 | Martz |
| 5,603,946 A | 2/1997 | Constantine |
| 5,605,546 A | 2/1997 | Wolzinger et al. |
| 5,616,387 A | 4/1997 | Augst et al. |
| 5,618,556 A | 4/1997 | Johns et al. |
| 5,622,711 A | 4/1997 | Chen |
| 5,633,010 A | 5/1997 | Chen |
| 5,637,080 A | 6/1997 | Geng |
| 5,639,469 A | 6/1997 | Benes et al. |
| 5,643,187 A | 7/1997 | N.ae butted.stoft et al. |
| 5,653,699 A | 8/1997 | Reed et al. |
| 5,670,557 A | 9/1997 | Dietz et al. |
| 5,674,523 A | 10/1997 | Cartmell et al. |
| 5,674,561 A | 10/1997 | Dietz et al. |
| 5,704,905 A | 1/1998 | Jensen et al. |
| 5,709,651 A | 1/1998 | Ward |
| 5,713,842 A | 2/1998 | Kay |
| 5,714,225 A | 2/1998 | Hansen et al. |
| 5,728,071 A | 3/1998 | Watson et al. |
| 5,733,251 A | 3/1998 | Johns |
| 5,733,570 A | 3/1998 | Chen et al. |
| 5,738,642 A | 4/1998 | Heinecke et al. |
| 5,750,134 A | 5/1998 | Scholz et al. |
| 5,750,136 A | 5/1998 | Scholz et al. |
| 5,755,681 A | 5/1998 | Plews |
| 5,780,045 A | 7/1998 | McQuinn et al. |
| 5,782,787 A | 7/1998 | Webster |
| 5,792,089 A | 8/1998 | Penrose et al. |
| 5,840,052 A | 11/1998 | Johns |
| 5,846,214 A | 12/1998 | Makuuchi et al. |
| 5,846,558 A | 12/1998 | Nielsen et al. |
| 5,849,325 A | 12/1998 | Heinecke et al. |
| 5,853,750 A | 12/1998 | Dietz et al. |
| 5,885,254 A | 3/1999 | Matyas |
| 5,887,590 A | 3/1999 | Price |
| D408,541 S | 4/1999 | Dunshee et al. |
| 5,891,076 A | 4/1999 | Fabo |
| D409,754 S | 5/1999 | Dunshee et al. |
| D410,087 S | 5/1999 | Dunshee et al. |

(56) References Cited

U.S. PATENT DOCUMENTS

| | | | |
|---|---|---|---|
| 5,939,339 A | 8/1999 | Delmore et al. |
| 5,941,840 A | 8/1999 | Court et al. |
| 5,947,917 A | 9/1999 | Carte et al. |
| 5,951,505 A | 9/1999 | Gilman et al. |
| 5,952,398 A | 9/1999 | Dietz et al. |
| 5,968,533 A | 10/1999 | Porter et al. |
| 5,973,221 A | 10/1999 | Collyer et al. |
| 5,976,117 A | 11/1999 | Dunshee et al. |
| 5,985,990 A | 11/1999 | Kantner et al. |
| 6,008,429 A | 12/1999 | Ritger |
| 6,043,408 A | 3/2000 | Geng |
| 6,090,076 A | 7/2000 | Lane, Jr. |
| 6,103,369 A | 8/2000 | Lucast et al. |
| D430,674 S | 9/2000 | Dunshee et al. |
| 6,121,508 A | 9/2000 | Bischof et al. |
| 6,124,520 A | 9/2000 | Roberts |
| 6,124,521 A | 9/2000 | Roberts |
| 6,129,971 A | 10/2000 | Brandt et al. |
| 6,139,868 A | 10/2000 | Hoffmann |
| 6,140,548 A | 10/2000 | Hansen et al. |
| 6,149,614 A | 11/2000 | Dunshee et al. |
| 6,168,800 B1 | 1/2001 | Dobos et al. |
| 6,169,224 B1 | 1/2001 | Heinecke et al. |
| 6,191,339 B1 | 2/2001 | Gueret |
| 6,197,397 B1 | 3/2001 | Sher et al. |
| 6,198,016 B1 | 3/2001 | Lucast et al. |
| 6,210,704 B1 | 4/2001 | Sasaki et al. |
| 6,225,521 B1 | 5/2001 | Gueret |
| 6,255,552 B1 | 7/2001 | Cummings et al. |
| 6,264,976 B1 | 7/2001 | Heinecke et al. |
| 6,302,867 B1 | 10/2001 | Brown, Jr. et al. |
| 6,309,500 B1 | 10/2001 | Jensen et al. |
| D454,955 S | 3/2002 | Dunshee et al. |
| 6,387,495 B1 | 5/2002 | Reeves et al. |
| 6,420,622 B1 | 7/2002 | Johnston et al. |
| 6,429,154 B1 | 8/2002 | Trotter |
| 6,436,432 B2 | 8/2002 | Heinecke et al. |
| 6,461,467 B2 | 10/2002 | Blatchford et al. |
| 6,468,383 B2 | 10/2002 | Kundel |
| 6,479,073 B1 | 11/2002 | Lucast et al. |
| 6,518,343 B1 | 2/2003 | Lucast et al. |
| D473,947 S | 4/2003 | Jacobson |
| 6,552,244 B1 | 4/2003 | Jacques et al. |
| D474,842 S | 5/2003 | Wolsing et al. |
| 6,566,575 B1 | 5/2003 | Stickels et al. |
| 6,566,577 B1 | 5/2003 | Addison et al. |
| 6,607,799 B1 | 8/2003 | Heinecke et al. |
| D480,144 S | 9/2003 | Adams et al. |
| D484,601 S | 12/2003 | Griffiths et al. |
| D484,602 S | 12/2003 | Griffiths et al. |
| 6,663,584 B2 | 12/2003 | Griesbach, III et al. |
| 6,680,113 B1 | 1/2004 | Lucast et al. |
| 6,685,682 B1 * | 2/2004 | Heinecke .......... A61F 13/023 602/41 |
| 6,727,402 B1 | 4/2004 | Bruss et al. |
| D492,411 S | 6/2004 | Bierman |
| 6,756,102 B1 | 6/2004 | Galo |
| 6,809,230 B2 | 10/2004 | Hancock et al. |
| 6,822,132 B2 | 11/2004 | Ahrens et al. |
| 6,827,707 B2 | 12/2004 | Wright et al. |
| 6,838,589 B2 | 1/2005 | Liedtke et al. |
| 6,841,715 B2 | 1/2005 | Roberts |
| D501,559 S | 2/2005 | Shaw et al. |
| 6,867,342 B2 | 3/2005 | Johnston et al. |
| D503,982 S | 4/2005 | Liedtke et al. |
| 6,878,385 B2 | 4/2005 | Jensen et al. |
| 6,888,042 B1 | 5/2005 | Freeman |
| 6,897,348 B2 | 5/2005 | Malik |
| 6,903,151 B2 | 6/2005 | Lucast et al. |
| 6,903,243 B1 | 6/2005 | Burton |
| 6,911,243 B2 | 6/2005 | Sher et al. |
| 6,927,315 B1 | 8/2005 | Heinecke et al. |
| D511,005 S | 10/2005 | Liedtke et al. |
| 6,955,659 B1 | 10/2005 | Carter |
| D512,509 S | 12/2005 | Yamasoto et al. |
| 6,987,209 B2 | 1/2006 | Augustine et al. |
| 6,994,904 B2 | 2/2006 | Joseph et al. |
| 6,998,511 B2 | 2/2006 | Worthley |
| 7,005,031 B2 | 2/2006 | Lucast et al. |
| D516,729 S | 3/2006 | Liedtke et al. |
| 7,030,288 B2 | 4/2006 | Liedtke et al. |
| 7,049,479 B2 | 5/2006 | Cleary et al. |
| D524,946 S | 7/2006 | Shaw et al. |
| 7,094,944 B2 | 8/2006 | Faasse, Jr. |
| 7,129,389 B1 | 10/2006 | Watson |
| 7,135,606 B1 | 11/2006 | Dozier et al. |
| 7,182,085 B1 | 2/2007 | Larsen et al. |
| 7,182,955 B2 | 2/2007 | Hart et al. |
| 7,183,454 B1 | 2/2007 | Rosenberg |
| D537,948 S | 3/2007 | Smith |
| 7,217,853 B2 | 5/2007 | Kulichikhin et al. |
| 7,223,899 B2 | 5/2007 | Sigurjonsson |
| D545,440 S | 6/2007 | Jensen |
| 7,232,454 B2 | 6/2007 | Rousseau |
| 7,279,177 B2 | 10/2007 | Looney et al. |
| 7,294,751 B2 | 11/2007 | Propp et al. |
| 7,294,752 B1 | 11/2007 | Propp |
| D557,424 S | 12/2007 | Knight |
| 7,304,202 B2 | 12/2007 | Sigurjonsson et al. |
| 7,316,840 B2 | 1/2008 | Neculescu et al. |
| 7,317,134 B2 | 1/2008 | Faasse, Jr. |
| 7,344,512 B2 | 3/2008 | Yamazaki et al. |
| D572,824 S | 7/2008 | Propp |
| D573,260 S | 7/2008 | Dunshee |
| 7,396,975 B2 | 7/2008 | Sigurjonsson et al. |
| 7,442,849 B2 | 10/2008 | Heinecke |
| 7,531,711 B2 | 5/2009 | Sigurjonsson et al. |
| 7,563,941 B2 | 7/2009 | Lebner et al. |
| 7,576,256 B2 | 8/2009 | Bjomberg et al. |
| 7,585,554 B2 | 9/2009 | Johnson et al. |
| D601,707 S | 10/2009 | Chouiller |
| 7,598,298 B2 | 10/2009 | Lewandowski et al. |
| 7,615,674 B2 | 11/2009 | Asherman |
| 7,624,869 B2 | 12/2009 | Primer |
| 7,626,070 B2 | 12/2009 | Propp |
| 7,674,948 B2 | 3/2010 | Propp et al. |
| 7,691,096 B2 | 4/2010 | Gillis |
| 7,723,561 B2 | 5/2010 | Propp |
| D620,123 S | 7/2010 | Igwebuike |
| 7,759,537 B2 | 7/2010 | Bishop et al. |
| 7,759,539 B2 | 7/2010 | Shaw et al. |
| 7,781,639 B2 | 8/2010 | Johnston et al. |
| 7,807,661 B2 | 10/2010 | Ylitalo et al. |
| 7,812,212 B2 | 10/2010 | Propp et al. |
| 7,858,838 B2 | 12/2010 | Holm et al. |
| 7,888,546 B2 | 2/2011 | Marcoux et al. |
| D634,423 S | 3/2011 | Heinecke et al. |
| 7,910,790 B2 | 3/2011 | Johnston et al. |
| 7,981,087 B2 | 7/2011 | Gesler, III |
| 7,988,673 B2 | 8/2011 | Wright et al. |
| 7,994,381 B2 | 8/2011 | Baron et al. |
| 8,002,113 B1 * | 8/2011 | Cummings .......... B65D 85/672 206/408 |
| 8,049,057 B2 | 11/2011 | Propp |
| 8,049,058 B2 | 11/2011 | Propp |
| 8,053,623 B2 | 11/2011 | Propp |
| 8,053,624 B2 | 11/2011 | Propp |
| 8,084,665 B2 | 12/2011 | Liedtke et al. |
| 8,093,445 B2 | 1/2012 | Sigurjonsson et al. |
| 8,110,718 B2 | 2/2012 | Heinecke |
| 8,158,845 B2 | 4/2012 | Qin et al. |
| 8,173,113 B1 | 5/2012 | Scholz et al. |
| 8,197,447 B2 * | 6/2012 | Wright ................ A61M 5/158 128/846 |
| 8,212,101 B2 | 7/2012 | Propp |
| 8,237,009 B2 | 8/2012 | Siniaguine |
| 8,247,635 B2 | 8/2012 | Sigurjonsson et al. |
| 8,269,059 B2 | 9/2012 | Wright et al. |
| D672,464 S | 12/2012 | Holm et al. |
| 8,344,201 B2 | 1/2013 | Madsen et al. |
| 8,372,051 B2 | 2/2013 | Scholz et al. |
| 8,404,921 B2 | 3/2013 | Lee et al. |
| D679,392 S | 4/2013 | Peterson et al. |
| D679,402 S | 4/2013 | Conrad-Vlasak et al. |

(56) References Cited

U.S. PATENT DOCUMENTS

| | | |
|---|---|---|
| D679,403 S | 4/2013 | Heinecke et al. |
| 8,409,157 B2 | 4/2013 | Haggstrom et al. |
| 8,410,332 B2 | 4/2013 | Burton et al. |
| 8,450,553 B2 | 5/2013 | Utterberg et al. |
| D683,858 S | 6/2013 | Smith |
| 8,486,004 B1 | 7/2013 | Propp |
| D687,555 S | 8/2013 | Peterson et al. |
| D688,377 S | 8/2013 | Heinecke et al. |
| 8,513,481 B2 | 8/2013 | Gergely et al. |
| D690,425 S | 9/2013 | Heinecke et al. |
| 8,530,022 B2 | 9/2013 | Fabo et al. |
| D693,010 S | 11/2013 | Mosa et al. |
| D695,901 S | 12/2013 | Heinecke et al. |
| 8,604,265 B2 | 12/2013 | Locke et al. |
| 8,663,171 B2 | 3/2014 | Tambourgi et al. |
| 8,672,905 B2 | 3/2014 | Riesinger |
| D704,343 S | 5/2014 | Inoo et al. |
| D710,017 S | 7/2014 | Mosa et al. |
| 8,764,714 B2 | 7/2014 | Fabo et al. |
| D712,046 S | 8/2014 | Igwebuike et al. |
| D712,549 S | 9/2014 | Igwebuike et al. |
| D712,550 S | 9/2014 | Igwebuike et al. |
| 8,906,815 B2 | 12/2014 | Moore et al. |
| 9,000,252 B2 | 4/2015 | Bradford et al. |
| D729,391 S | 5/2015 | Igwebuike et al. |
| 9,029,625 B2 | 5/2015 | Effing et al. |
| 9,168,180 B2 * | 10/2015 | Ha ............ A61F 13/02 |
| 2001/0027285 A1 | 10/2001 | Heinecke et al. |
| 2001/0031370 A1 | 10/2001 | Kundel |
| 2001/0051178 A1 | 12/2001 | Blatchford et al. |
| 2002/0082540 A1 | 6/2002 | Johnston et al. |
| 2002/0128578 A1 | 9/2002 | Johnston et al. |
| 2003/0007999 A1 | 1/2003 | Blatchford et al. |
| 2003/0125680 A1 | 7/2003 | Ding |
| 2004/0133143 A1 | 7/2004 | Burton et al. |
| 2004/0143220 A1 * | 7/2004 | Worthley ............ A61M 25/02 |
| | | 604/174 |
| 2004/0158209 A1 | 8/2004 | Wright |
| 2004/0247654 A1 | 12/2004 | Asmus et al. |
| 2004/0247655 A1 | 12/2004 | Asmus et al. |
| 2005/0080372 A1 | 4/2005 | Nielsen et al. |
| 2005/0228352 A1 | 10/2005 | Heinecke et al. |
| 2006/0003133 A1 | 1/2006 | Johnson |
| 2006/0064049 A1 | 3/2006 | Marcussen |
| 2007/0027423 A1 * | 2/2007 | Scheinberg ............ A61F 13/06 |
| | | 602/54 |
| 2007/0060892 A1 | 3/2007 | Propp |
| 2007/0073211 A1 | 3/2007 | Propp |
| 2007/0078400 A1 | 4/2007 | Gesler |
| 2007/0106265 A1 | 5/2007 | Gillis |
| 2007/0156075 A1 | 7/2007 | Heinecke |
| 2007/0179419 A1 | 8/2007 | Simpson |
| 2008/0058692 A1 | 3/2008 | Propp et al. |
| 2008/0063695 A1 | 3/2008 | Vitaris |
| 2008/0132821 A1 | 6/2008 | Propp et al. |
| 2008/0281245 A1 | 11/2008 | Effing et al. |
| 2008/0312574 A1 | 12/2008 | Pernot |
| 2009/0082710 A1 | 3/2009 | Vitaris |
| 2009/0187130 A1 | 7/2009 | Asmus et al. |
| 2009/0192470 A1 | 7/2009 | Propp |
| 2009/0247965 A1 | 10/2009 | Williams |
| 2010/0004680 A1 | 1/2010 | Propp |
| 2010/0106113 A1 | 4/2010 | Heinecke |
| 2010/0106114 A1 * | 4/2010 | Weston ............ A61M 1/0088 |
| | | 604/319 |
| 2010/0121282 A1 | 5/2010 | Propp |
| 2010/0159192 A1 | 6/2010 | Cotton |
| 2010/0160866 A1 | 6/2010 | Propp |
| 2010/0198161 A1 | 8/2010 | Propp |
| 2010/0198162 A1 | 8/2010 | Propp |
| 2010/0318013 A1 | 12/2010 | Fabo et al. |
| 2010/0318052 A1 | 12/2010 | Ha et al. |
| 2010/0318072 A1 | 12/2010 | Johnston et al. |
| 2011/0004139 A1 | 1/2011 | Pigg |
| 2011/0015556 A1 | 1/2011 | Fabo et al. |
| 2011/0052665 A1 | 3/2011 | Hardy et al. |
| 2011/0098622 A1 | 4/2011 | Hatanaka et al. |
| 2011/0130738 A1 | 6/2011 | Schmidt |
| 2011/0166492 A1 | 7/2011 | Holm et al. |
| 2011/0257574 A1 | 10/2011 | Svensby |
| 2011/0280926 A1 | 11/2011 | Junginger |
| 2011/0282292 A1 | 11/2011 | Polowy et al. |
| 2012/0010572 A1 | 1/2012 | Bennett |
| 2012/0083723 A1 | 4/2012 | Vitaris et al. |
| 2012/0109069 A1 | 5/2012 | Dickert et al. |
| 2012/0109070 A1 | 5/2012 | Elsamahy et al. |
| 2012/0150122 A1 | 6/2012 | Harper |
| 2012/0197206 A1 | 8/2012 | Glenn |
| 2012/0238932 A1 | 9/2012 | Atteia et al. |
| 2013/0018322 A1 * | 1/2013 | Wright ............ A61F 13/023 |
| | | 604/180 |
| 2013/0053747 A1 | 2/2013 | Lin |
| 2013/0102945 A1 | 4/2013 | Long |
| 2013/0138063 A1 | 5/2013 | Wiltshire et al. |
| 2013/0150796 A1 | 6/2013 | Souza et al. |
| 2013/0152944 A1 | 6/2013 | Okada et al. |
| 2013/0165865 A1 | 6/2013 | Kelvered et al. |
| 2013/0172843 A1 | 7/2013 | Kurata |
| 2013/0211347 A1 | 8/2013 | Arbel et al. |
| 2013/0218085 A1 | 8/2013 | Knobloch |
| 2013/0220347 A1 | 8/2013 | Al Otaibi |
| 2013/0281906 A1 | 10/2013 | Fabo et al. |
| 2013/0310754 A1 | 11/2013 | Kutsch |
| 2013/0317405 A1 | 11/2013 | Ha et al. |
| 2013/0317406 A1 | 11/2013 | Locke et al. |
| 2014/0005607 A1 | 1/2014 | Elsamahy et al. |
| 2014/0058309 A1 | 2/2014 | Addison et al. |
| 2014/0066867 A1 | 3/2014 | Locke et al. |
| 2014/0107561 A1 | 4/2014 | Dorian et al. |
| 2014/0121638 A1 | 5/2014 | Mosa et al. |
| 2014/0121649 A1 | 5/2014 | Calco |
| 2014/0142490 A1 | 5/2014 | Johannison |
| 2014/0142526 A1 | 5/2014 | Auguste et al. |
| 2014/0158572 A1 | 6/2014 | Jensen |
| 2014/0243728 A1 | 8/2014 | Igwebuike et al. |
| 2014/0249495 A1 | 9/2014 | Mumby et al. |
| 2014/0257242 A1 | 9/2014 | Sung |
| 2014/0316353 A1 | 10/2014 | Riesinger |
| 2015/0005688 A1 | 1/2015 | Goby |
| 2015/0088085 A1 | 3/2015 | Rovaniemi |
| 2015/0141949 A1 | 5/2015 | Decabooter et al. |
| 2015/0157509 A1 | 6/2015 | Atkinson et al. |
| 2015/0209188 A1 | 7/2015 | Scheremet et al. |

FOREIGN PATENT DOCUMENTS

| | | |
|---|---|---|
| EP | 424165 A1 | 4/1991 |
| EP | 919211 A2 | 6/1999 |
| GB | 1457164 A | 12/1976 |
| WO | 1984003837 A1 | 10/1984 |
| WO | 1992016245 A1 | 10/1992 |
| WO | 1994012134 A1 | 6/1994 |
| WO | 1994021207 A2 | 9/1994 |
| WO | 1998000080 A1 | 1/1998 |
| WO | 1998015245 A1 | 4/1998 |
| WO | 1999006077 A1 | 2/1999 |
| WO | 1999027975 A1 | 6/1999 |
| WO | 01/49233 A1 | 7/2001 |
| WO | 02/20067 A2 | 3/2002 |
| WO | 02/34304 A1 | 5/2002 |
| WO | 03/80133 A1 | 10/2003 |
| WO | 2004/026389 A2 | 4/2004 |
| WO | 2007034393 A2 | 3/2007 |
| WO | 2009/075636 A1 | 6/2009 |
| WO | 2012083965 A1 | 6/2012 |
| WO | 2012125530 A1 | 9/2012 |
| WO | 2013/057508 A1 | 4/2013 |
| WO | 2013082883 A1 | 6/2013 |
| WO | 2013096027 A1 | 6/2013 |
| WO | 2013162680 A1 | 10/2013 |
| WO | 2013173588 A1 | 11/2013 |
| WO | 2014020440 A1 | 2/2014 |
| WO | 2014020443 A2 | 2/2014 |
| WO | 2014051040 A1 | 4/2014 |

(56) References Cited

FOREIGN PATENT DOCUMENTS

| WO | 2014081626 A1 | 5/2014 |
|---|---|---|
| WO | 2014097069 A1 | 6/2014 |
| WO | 2014099709 A1 | 6/2014 |
| WO | 2014120746 A1 | 8/2014 |
| WO | 2015022334 A1 | 2/2015 |
| WO | 2015022340 A1 | 2/2015 |
| WO | 2015050749 A1 | 4/2015 |
| WO | 2015102981 A1 | 7/2015 |
| WO | 2015130608 A1 | 9/2015 |
| WO | 2016/040695 A1 | 3/2016 |

OTHER PUBLICATIONS

3M "3M Tegaderm and Tegaderm HP Transparent Dressings" 2005.
3M "3M Tegaderm IV Advanced Securement Dressings", (1 of 2) 2011.
3M "3M Tegaderm IV Advanced Securement Dressings", (2 of 2) 2011.
3M "Tegaderm Full Line of IV Site Dressings" brochure. 2012.
3M Tegaderm Transparent Dressing—2-3/8x2-3/4in., 2013.
3M Tegaderm Transparent Dressing—4x4,3/4in., 2013.
3M Tegaderm Transparent Dressing—6x8in., 2013.
3M Tegaderm Transparent Dressing—Film Roll, 2005.
3M Tegaderm Transparent Dressing—Notched 4x4,3/4in., 2013.
3M Tegaderm Transparent Dressing FAQ Jan. 26, 2007.
3M Tegaderm Transparent Dressing I.F.U. 1999.
Centurion "Dressings and securement products" brochure. 2011.
Medline "Today's wound care treatments", Jun. 2012.
Molnlychke Health Care "Mepore Film, formerly Mefilm", 2007.
PCT/US2015/049517 filed Sep. 10, 2015 International Search Report and Written Opinion dated Jan. 21, 2016.
EP 15839400.7 filed Mar. 16, 2017 Extended European Search Report dated Mar. 16, 2018.
EP 15839400.7 filed Mar. 16, 2017 Partial European Search Report dated Mar. 16, 2018.

* cited by examiner

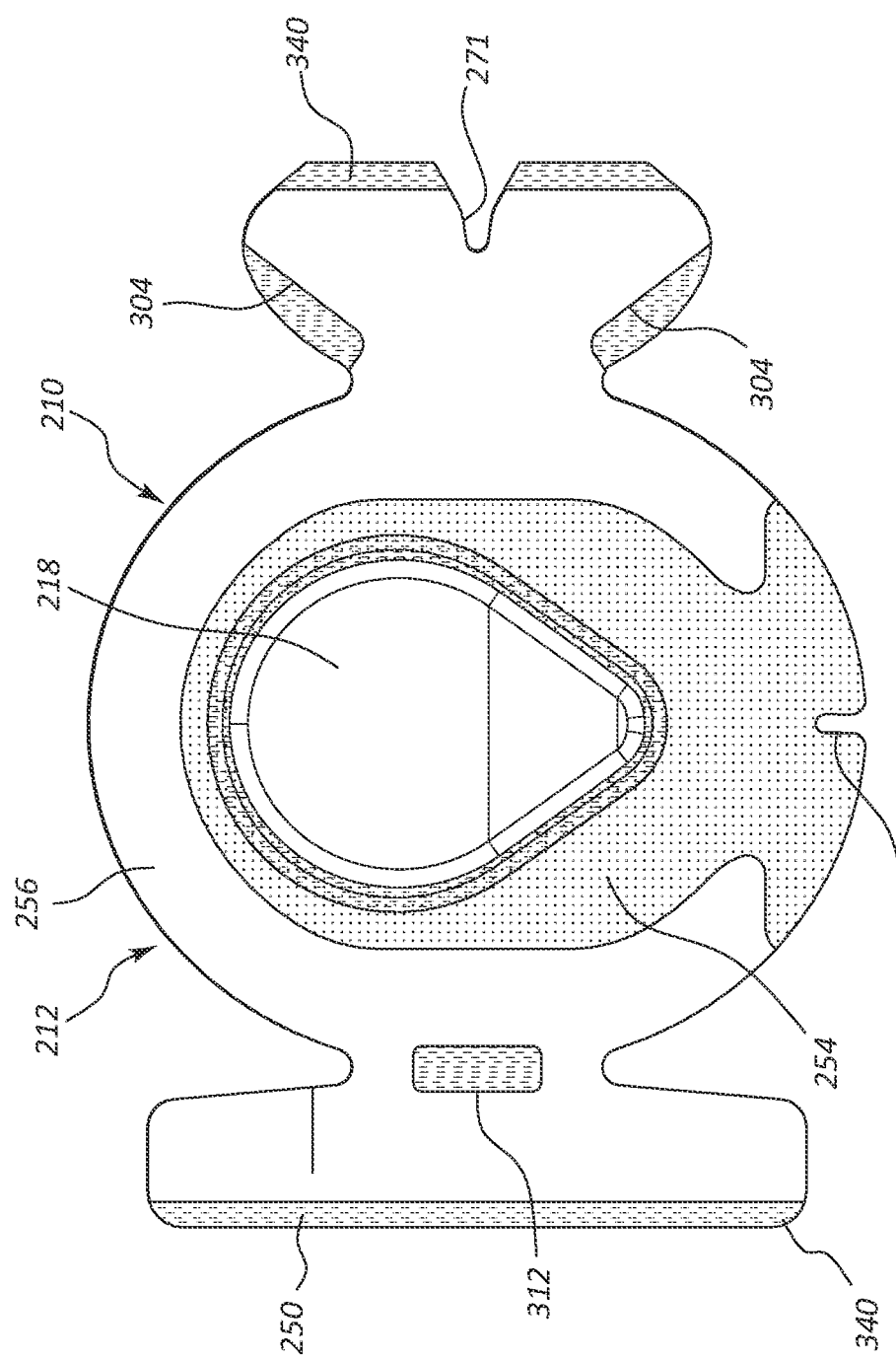

PROTECTIVE DRESSING FOR SKIN-PLACED MEDICAL DEVICE

CROSS-REFERENCE TO RELATED APPLICATIONS

This application claims the benefit of U.S. Provisional Patent Application No. 62/048,747, filed Sep. 10, 2014, and titled "Protective Dressing For Skin-Placed Medical Device," which is incorporated herein by reference in its entirety.

BRIEF SUMMARY

Briefly summarized, embodiments of the present invention are directed to a dressing for use in protectively covering a medical device placed on and/or through the skin surface of a patient. Examples of such devices include infusion needles for accessing subcutaneously implanted access ports, catheters of various types and purposes, insulin infusion needles, etc. When placed atop the skin-placed medical device, the dressing prevents bacteria and other undesired microbes or external contaminants from reaching the medical device and its insertion site through the skin. Further, the dressing is configured such that water vapor may be transmitted therethrough, thus enabling the insertion site to breathe and prevent undesired moisture buildup under the dressing.

In one embodiment, a dressing for covering a medical device on a skin surface of a patient is disclosed and comprises a dressing portion that is configured to rest against a skin surface of a patient, with the dressing portion defining a hole, and a polymeric cover film that is at least indirectly attached to the dressing portion. The cover film includes a pliable domed portion aligned with the hole of the dressing portion. The pliable domed portion defines a cavity that configured to receive therein the medical device when the dressing is placed on the skin of the patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 16 is a top view of a portion of the medical device dressing of FIGS. 6A-6D;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a dressing for use in protectively covering a medical device placed on and/or through the skin surface of a patient. Examples of such devices include infusion needles for accessing subcutaneously implanted access ports, catheters of various types and purposes, insulin infusion needles, etc. When placed atop the skin-placed medical device, the dressing prevents bacteria and other undesired microbes or external contaminants from reaching the medical device and its insertion site through the skin. Further, the dressing is configured such that water vapor may be transmitted therethrough, thus enabling the insertion site to breathe and prevent undesired moisture buildup under the dressing.

In accordance with one embodiment, the dressing is shaped and configured so as to suitably cover medical devices that extend some distance above the skin surface without causing deformation, "tenting," and/or peel-away of the dressing from the skin due to tension between the dressing surface and the medical device. In addition, the dressing includes a pliable domed cover that can cover the medical device, conform to the medical device if necessary, and deform when contacted so as to enhance patient comfort, all while providing isolation for the medical device from potential contaminants. In one embodiment, the domed cover also assists in securing the medical device in place on the patient skin.

Figure 1A:
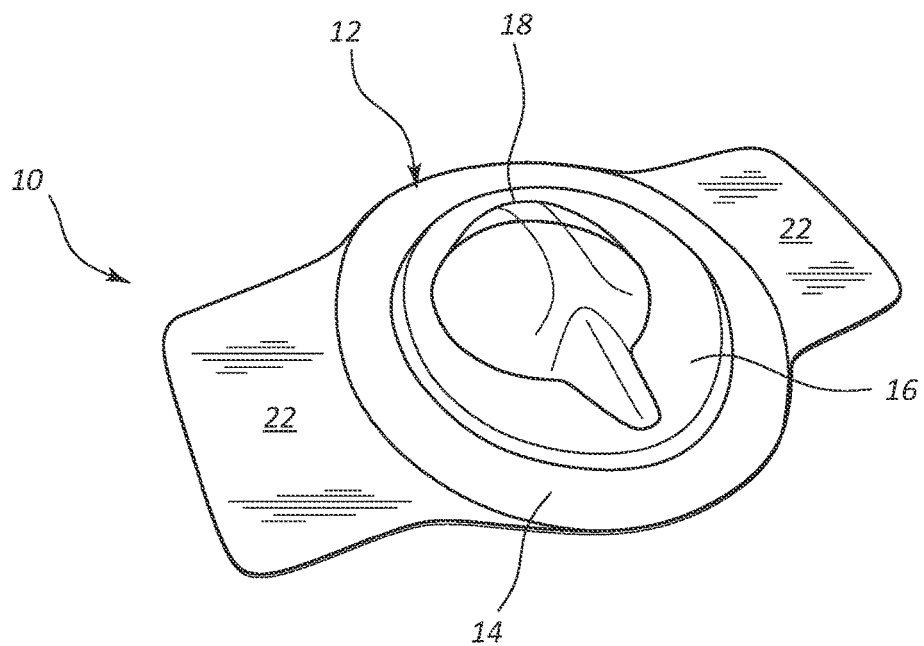
FIGS. 1A and 1B are various views of a medical device dressing according to one embodiment.
Figure 1B:
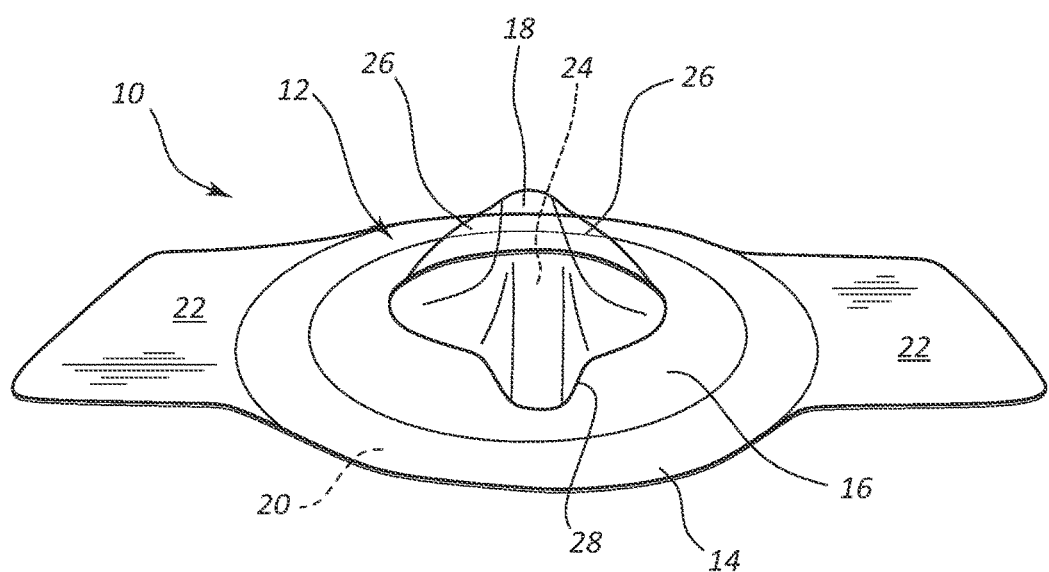

Reference is first made to FIGS. 1A and 1B, which show various views of a dressing for a medical device ("dressing"), generally designated at 10, according to one embodiment. As shown, the dressing 10 includes a body 12 that in turn includes a perimeter portion 14 surrounding a central portion 16. The perimeter portion 14 provides a barrier and boundary for the dressing 10 by adhering to the skin of the patient about a medical device placed on the skin or through the skin via an insertion site. As such, the perimeter portion 14 includes in the present embodiment an adhesive 20 on its bottom, skin-contacting surface so as to easily adhere to the skin surface when placed by a clinician over a medical device. In another embodiment, the dressing 10 can be attached to the skin without covering a medical device, such as in the case of covering a wound, incision, etc.

In the present embodiment, the perimeter portion 14 includes a suitably strong yet bendable material such as a non-woven fabric including polyester or other suitable material. Though shown as circular, the shape of the perimeter portion 14 can include other shapes, such as square, oval, triangular, etc.

The dressing 10 further includes a central portion 16 that is pliable and breathable so as to enable moisture transfer therethrough and prevent undesired moisture buildup underneath the dressing 10. As such, in the present embodiment the central portion 16 includes polyurethane or other suitable thermoplastic or material that possesses a relatively high moisture vapor transfer rate ("mvtr") so as to enable suitable moisture transmission therethrough. In one embodiment, a polyurethane sheet with a thickness of between about 0.8 mil to about 2 mils is employed for the central portion 16, though it is appreciated that other sheet thicknesses of differing moisture vapor transfer rates can be employed, including low mvtr values.

In the present embodiment, the central portion 16 is suitably transparent to enable inspection of the medical device/insertion site under the dressing 10 to be made from outside the dressing. Use of a polyurethane central portion provides such transparency, as do other suitable thermoplastics. In another embodiment, the central portion 16 is semi-transparent or opaque.

FIGS. 1A and 1B further show that the central portion 16 of the dressing 10 includes a pliable, domed portion 18 that is raised with respect to the surrounding portions of the dressing. The raised nature of the domed portion 18 defines a cavity 24 under the domed portion that can be occupied by the infusion needle or other medical device when the dressing 10 is placed over the device. This enables the dressing 10 to suitably cover and isolate the infusion needle disposed beneath the central portion 16 without significant, undesired deformation of the dressing, which is common in known dressings. Such undesired deformation of the dressing includes "tenting," in which the dressing is deformed into a pointed or spiked configuration, which causes a separation force that can result in the pulling away of the perimeter of the adhesively adhered dressing from engagement with the skin, thus possibly compromising the isolating nature of the dressing and providing an undesired entry pathway for microbes into the dressing interior. Tenting is thus an example of undesired dressing deformations that are prevented by virtue of the three-dimensionally raised nature of the domed portion 18 of the present dressing 10.

Because it is manufactured from the pliable material of the central portion 16, the domed portion 18, though given a raised configuration so as to extend away from the patient skins, is collapsible in this and other embodiments as to increase patient comfort.

As part of the central portion 16, the domed portion 18 in the present embodiment includes the same material as the central portion (such as polyurethane), though in other embodiments the domed portion can include a material that differs from other portions of the dressing 10, including the central portion. Further, in the present embodiment the underside of the regions of the central portion 16 that surround the domed portion include the adhesive 20 (as does the underside of the perimeter portion 14) so as to adhere to the skin when the dressing 10 is placed thereon, while the domed portion 18 includes no such adhesive so it can remain raised from the skin surface and not interfere with the medical device. In other embodiments, the configuration of adhesive application can vary, such as the application of adhesive to the underside of the domed portion 18 so as to adhere the domed portion to the medical device it covers. It is also appreciated that one or more antimicrobial agents can be applied to the underside or other suitable portions of the dressing so as to prevent the formation of microbes. In one embodiment, the antimicrobial agent can include silver, chlorhexidine gluconate ("CHG"), isopropyl alcohol ("IPA"), etc. Further details regarding antimicrobial agents that may be used according to one embodiment are found in U. S. Patent Application Publication No. 2013/0110025, filed Jul. 4, 2011, and entitled "Dressing Device for Use with a Cannula or a Catheter," which is incorporated herein by reference in its entirety.

As seen in FIGS. 1A and 1B, the domed portion 18 is shaped in one embodiment to correspond to the shape of a medical device, such as a particular infusion set, that is placed on the skin to be covered by the dressing 10. In the illustrated embodiment, for instance, the domed portion 18 includes indentations 26 to conform to a particular shape of an infusion set having a raised central hub. It is appreciated that the particular size, shape, and other configuration of the domed portion 18 can vary from what is shown and described herein. Further, the domed portion can be shaped to define a hemispherical cavity or other three-dimensional volume, including square, triangular, oval, oblong, and various other geometric and non-geometric shapes. As such, the term "domed portion" is understood to include a variety of shapes as formed by the pliable material of the central portion of the dressing, described above.

FIGS. 1A and 1B further show that the dressing 10 includes release liners 22 that protect the adhesive underside of the dressing and that are removed by the user before placing the dressing on the patient's skin. The domed portion 18 further defines a convergence, or point 28, in the present embodiment. The point 28 provides a visual cue for the clinician so as to place the dressing at a desired orientation on the skin of the patient. The point 28 further gives the dome portion a teardrop-shaped perimeter, in one embodiment. In the present embodiment, for instance, the point 28 corresponds with the direction of extension of the infusion set tubing from the infusion set. The tubing can then extend under the perimeter portion 14 where the adhesive on the underside of the perimeter portion seals about the tubing to isolate the cavity 24 of the domed portion 18.

Figure 2:
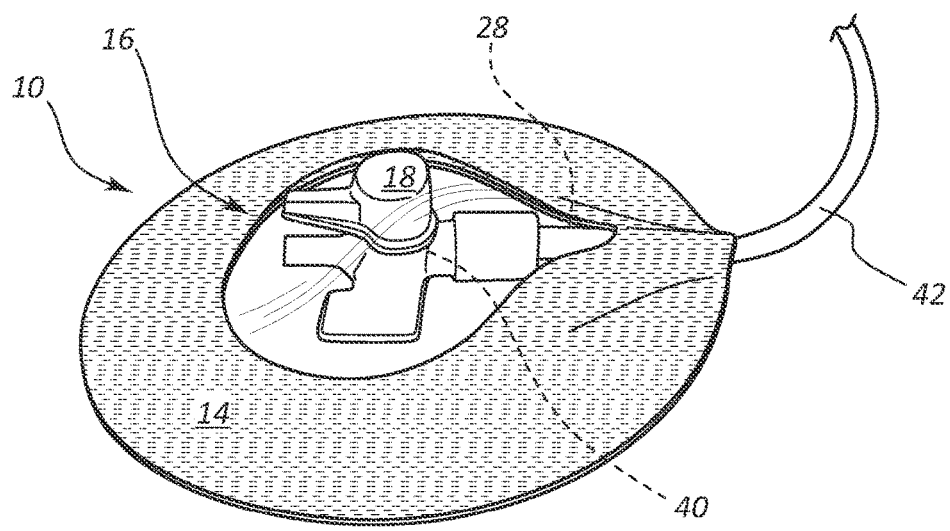
FIG. 2 is a perspective view of a medical device dressing in place atop a medical device according to one embodiment.

FIG. 2 shows a dressing 10 according to one embodiment, in place atop a medical device that in turn is placed atop a skin surface of a patient. The medical device on the illustrated embodiment is a ported IV catheter 40, though many other medical devices could be used with the dressing 10. As shown and because of its raised domed portion 18, the central portion 16 of the dressing 18 does not undesirably tent up so as to pull the perimeter portion 14 away from the skin 30 of the patient. Note that the tubing 42 of the catheter 40 is aligned with the point 28 of the domed portion 18 to further prevent undesired tenting of the central portion 16. Note also that the size, shape, color, placement, and other configuration aspects of the dressing can vary from what is shown and described herein while still residing within the principles of the present disclosure.

It is appreciated that the shape, size, and configuration of the domed portion 18 of the dressing 10 and other dressing described herein can be modified as needed to cover differing types and sizes of infusion needles, catheters, infusion pumps, and other medical devices. As such, each domed portion can be uniquely shaped to fit over the corresponding infusion set/medical device. In another embodiment, the domed portion is universally sized to fit a variety of infusion needles or other medical devices. Of course, the particular shapes and sizes of the domed portion 18 can vary from what is shown and described herein. In yet another embodiment, the dressing can include more than one domed portion to cover multiple medical devices placed on the patient's skin.

Figure 3:
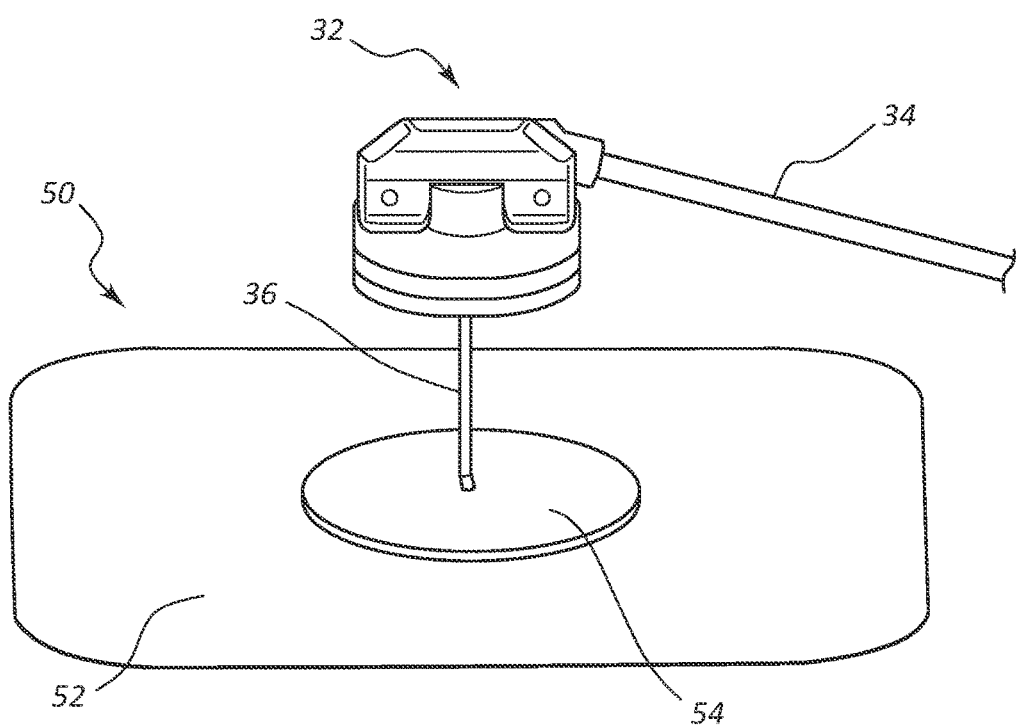
FIG. 3 is a perspective view of a portion of a medical device and a dressing according to one embodiment.

FIG. 3 depicts a dressing 50 according to one embodiment, including a pliable, film-like body 52 including polyurethane or other suitable material, and a foam pad 54 disposed atop the body. In the present embodiment, the foam pad 54 is attached to the top surface of the dressing body 52 via adhesive or the like. The foam pad 54 can carry an antimicrobial substance, such as CHA, IPA, etc. An infusion needle assembly 32 is shown with a needle 34 thereof penetrating the foam pad 54 and body 52 of the dressing 50 when the dressing has been placed on the patient skin prior to insertion of the infusion needle. The dressing 50 thus covers and protects the skin insertion site of the needle 36 of the infusion needle assembly 32.

Figure 4A:
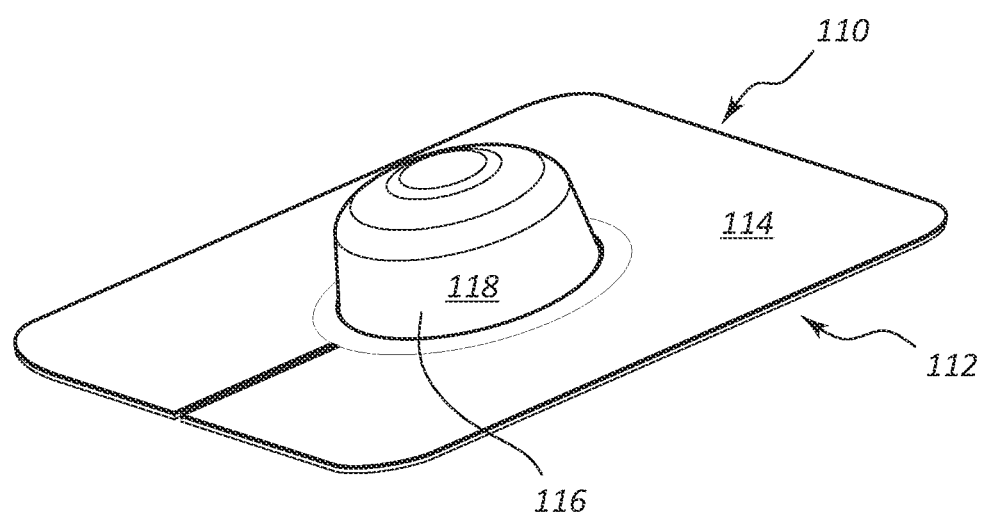
FIGS. 4A and 4B are various views of a medical device dressing according to one embodiment.
Figure 4B:
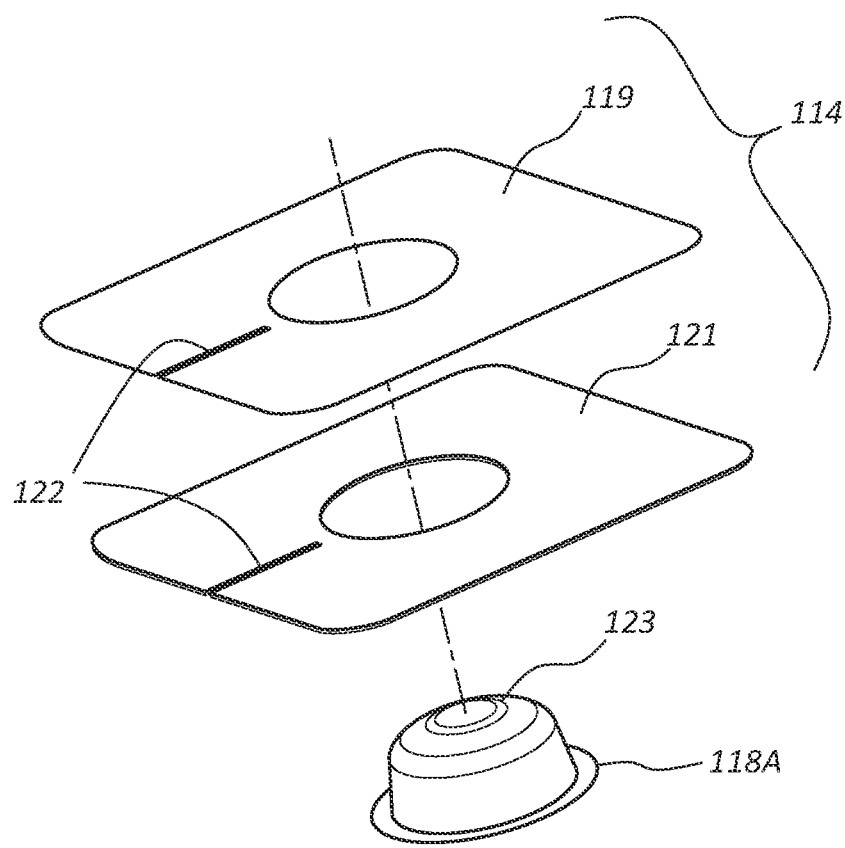

FIGS. 4A and 4B depict a dressing 110 according to another embodiment, including a body 112 that in turn includes a perimeter portion 114 and a central portion 116. The central portion 116 includes a domed portion 118 shaped to provide an interior cavity for covering a skin-placed medical device. The perimeter portion 114 includes a polyurethane or other suitable film 119 coupled to and atop a substantially flat, non-woven or other suitable material 121 to provide sturdiness to the dressing. An adhesive is applied to an underside of the material 121 so as to enable the dressing 110 to adhere to the skin. A slit 122 is provided to enable tubing or similar component to extend out of the dressing 110.

The domed portion 118 is separately formed with respect to the perimeter portion 114 in the present embodiment, is pliable, and includes a lip 118A to enable it to be secured via adhesive or other fixation within a hole defined in the perimeter portion 114. The domed portion 118 can include shape features 123 that provide some rigidity and/or reinforcement thereto. Note that, despite its name, the central portion in this and other embodiments can be placed in a non-centered location with respect to the dressing body.

In one embodiment, it is appreciated that one or more reinforcement features can extend across the domed portion of the dressings described herein to provide some rigidity and/or reinforcement thereto. The reinforcement feature can include, for instance, an adhesive strip, non-woven material that is bonded to the domed portion 218, etc.

Figure 6A:
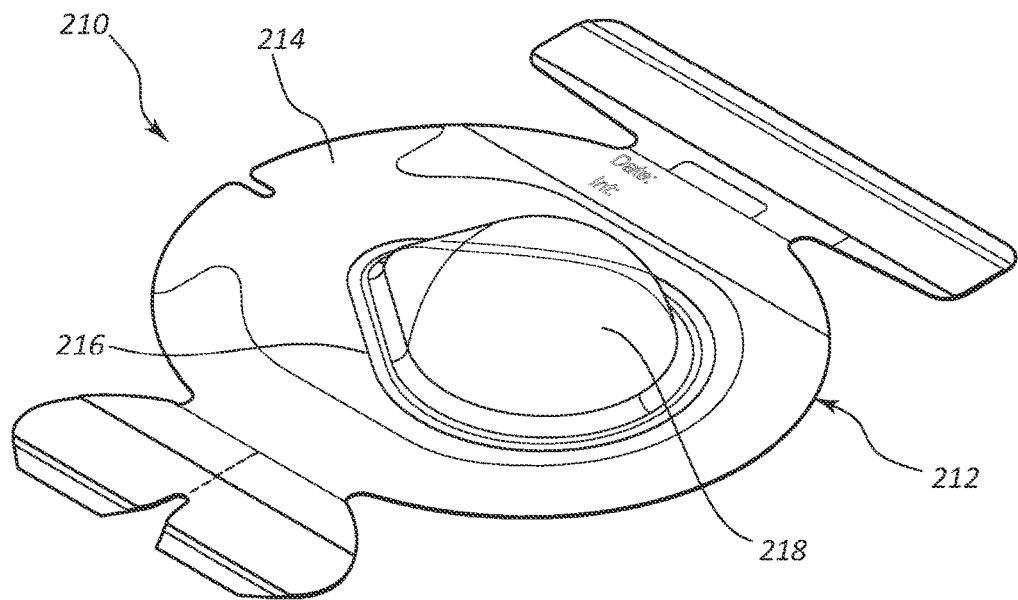
FIGS. 6A-6D are various views of a medical device dressing according to one embodiment.
Figure 6B:
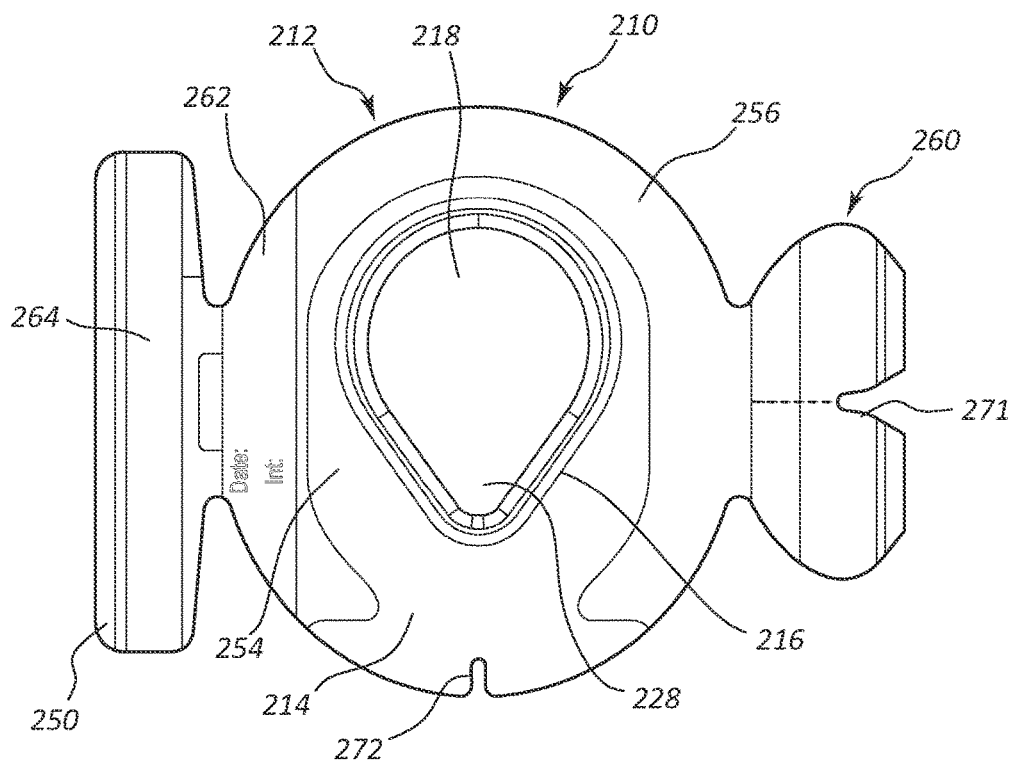
Figure 6C:
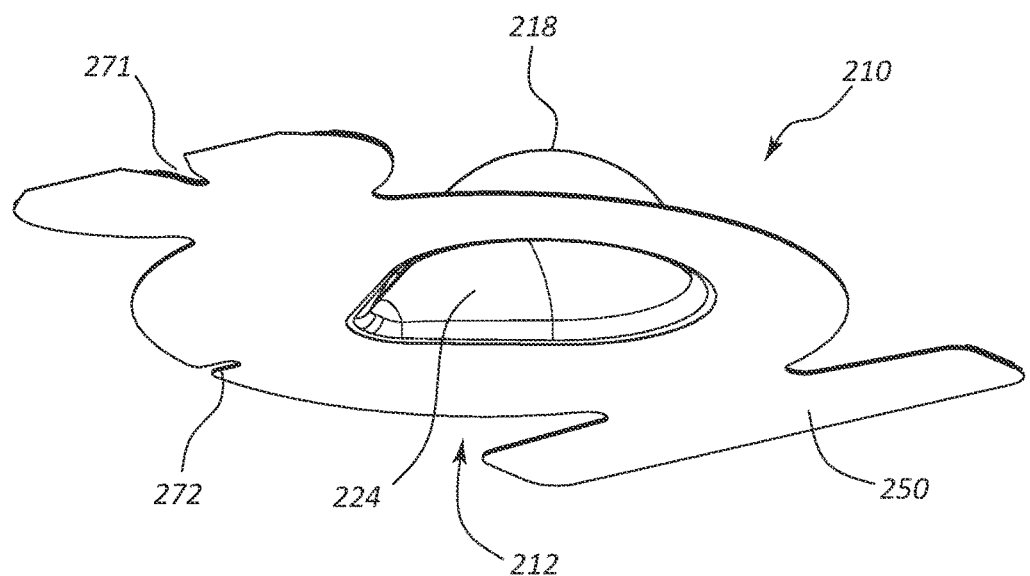
Figure 6D:
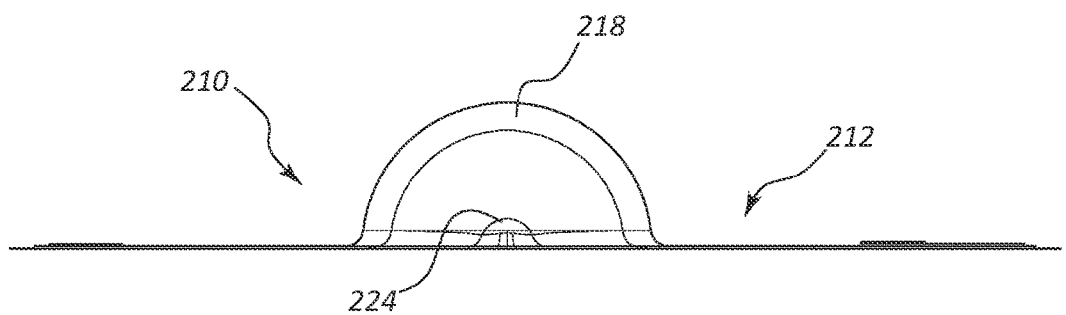
Figure 7:
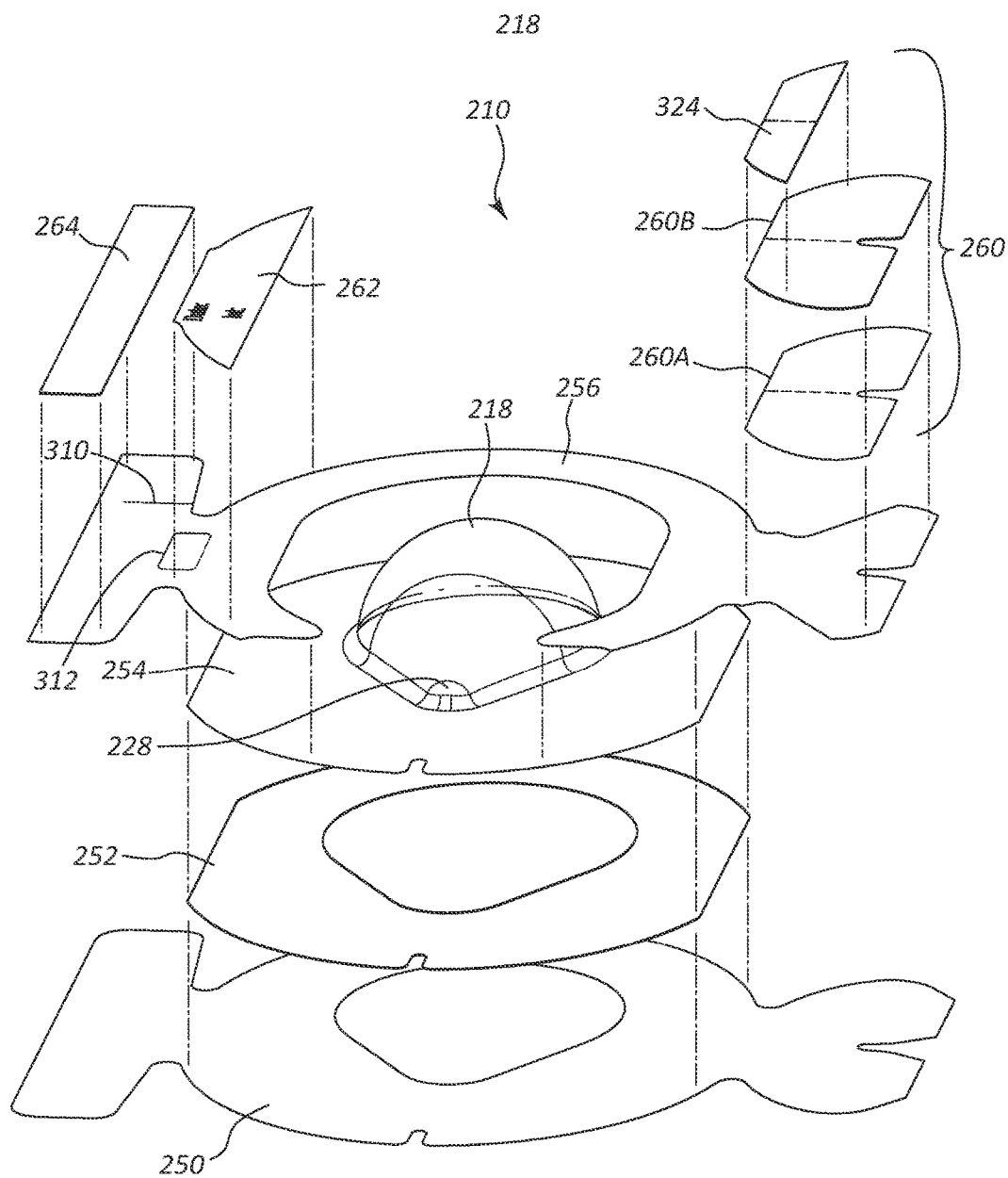
FIG. 7 is an exploded view of the medical device dressing of FIGS. 6A-6D.
Figure 8A:
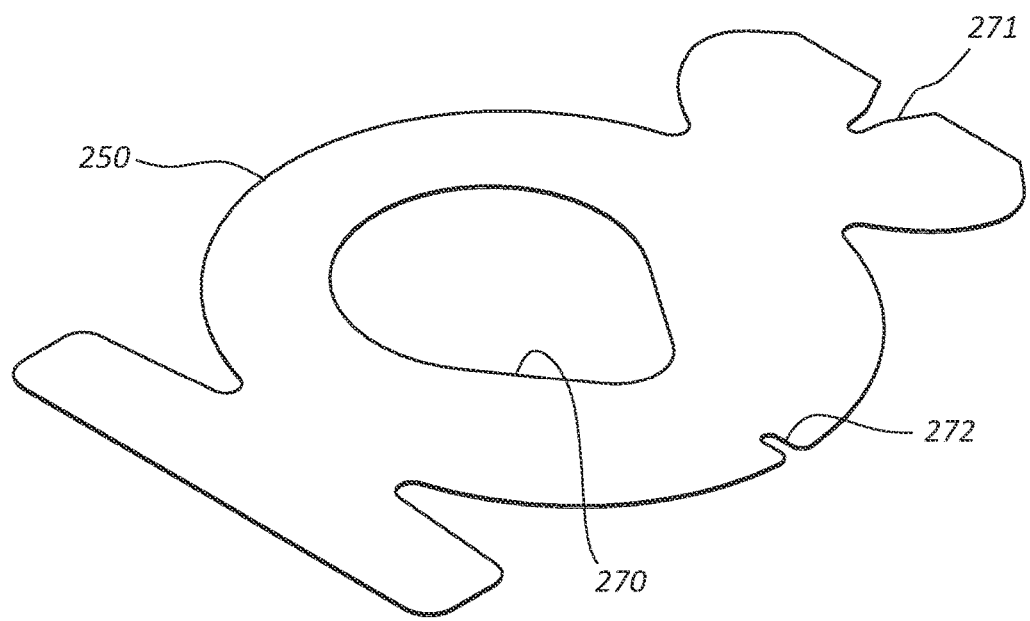
FIGS. 8A and 8B show various views of a portion of the medical device dressing of FIGS. 6A-6D.
Figure 8B:
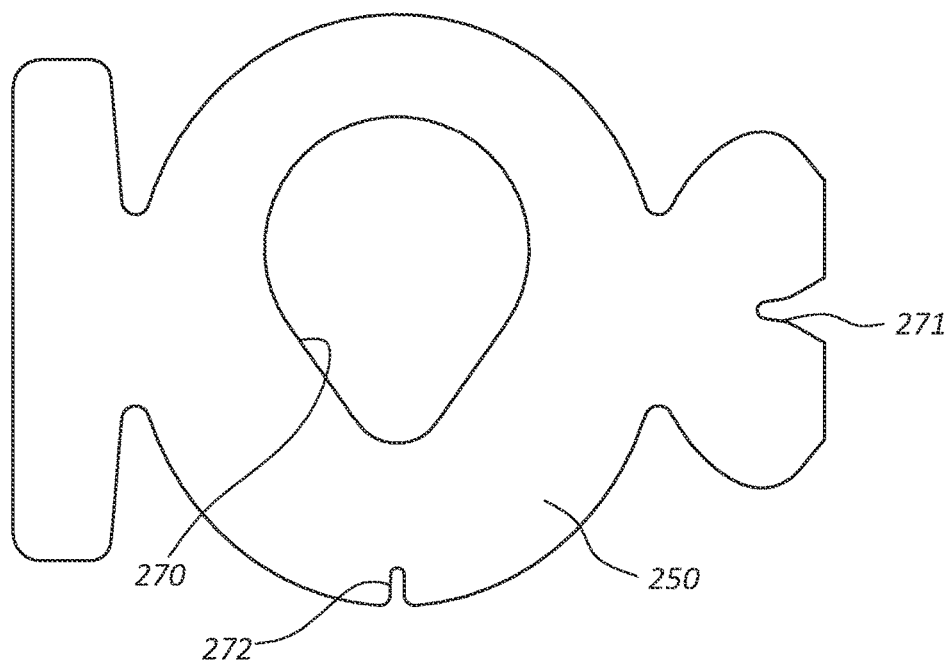

Reference is now made to FIGS. 6A-7, which depict a dressing 210 according to another embodiment. As shown, the dressing 210 including a body 212 that in turn includes a perimeter portion 214 and a central portion 216. The central portion 216 includes a domed portion 218 shaped to define an interior cavity 224 for covering a skin-placed medical device. As best seen in FIG. 6B, the domed portion includes a point 228 for providing adequate space in the cavity 224 for an infusion needle assembly or other medical device to be disposed therein and to assist in indicating to the clinician in which direction the tubing of the infusion needle assembly should extend.

In the present embodiment, the dressing 210 includes a plurality of layers as will be further described below. As seen in FIGS. 6C and 7, 8A, and 8B, a release liner 250 is included on the bottom of the dressing 210 (from the perspective shown in FIG. 7) that prevents undesired adhesion of the dressing to another surface prior to placement thereof on the skin of the patient. The release liner 250 in the present embodiment includes a super-calendered 50 weight craft paper with a silicone coating thereon, though other suitable materials can also be acceptably used, including other papers, polymeric materials, etc.

The release liner 250 includes a hole 270 defining a shape corresponding to domed portion 218. A first notch 271 is included at the side edge of the release liner 250, while a second notch 272 is included in the release liner proximate the portion of the hole 270 corresponding to the point 228 of the domed portion 218. Generally, the shape of the release liner 250 and the position and configuration of the above-named aspects of the release liner are supportive of other dressing components, as discussed below.

Figure 9A:
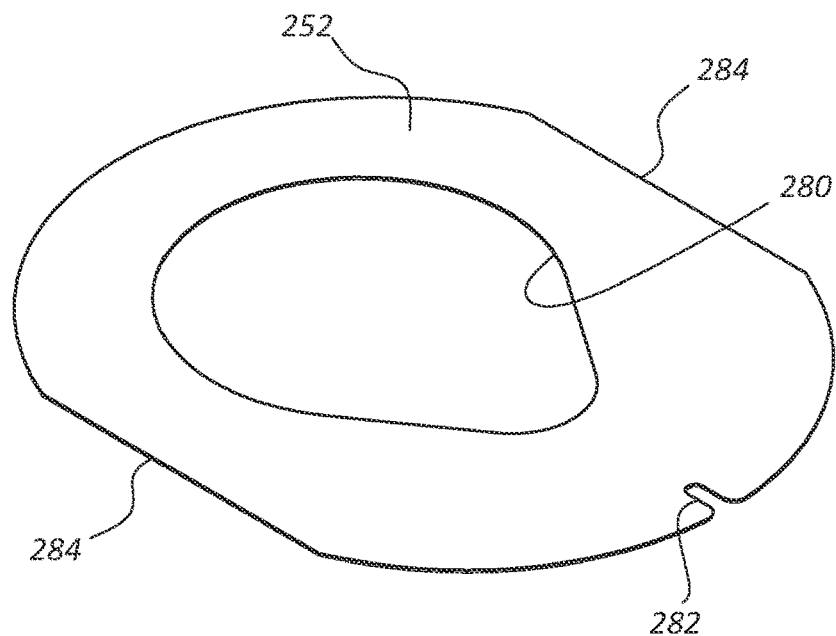
FIGS. 9A and 9B show various views of a portion of the medical device dressing of FIGS. 6A-6D.
Figure 9B:
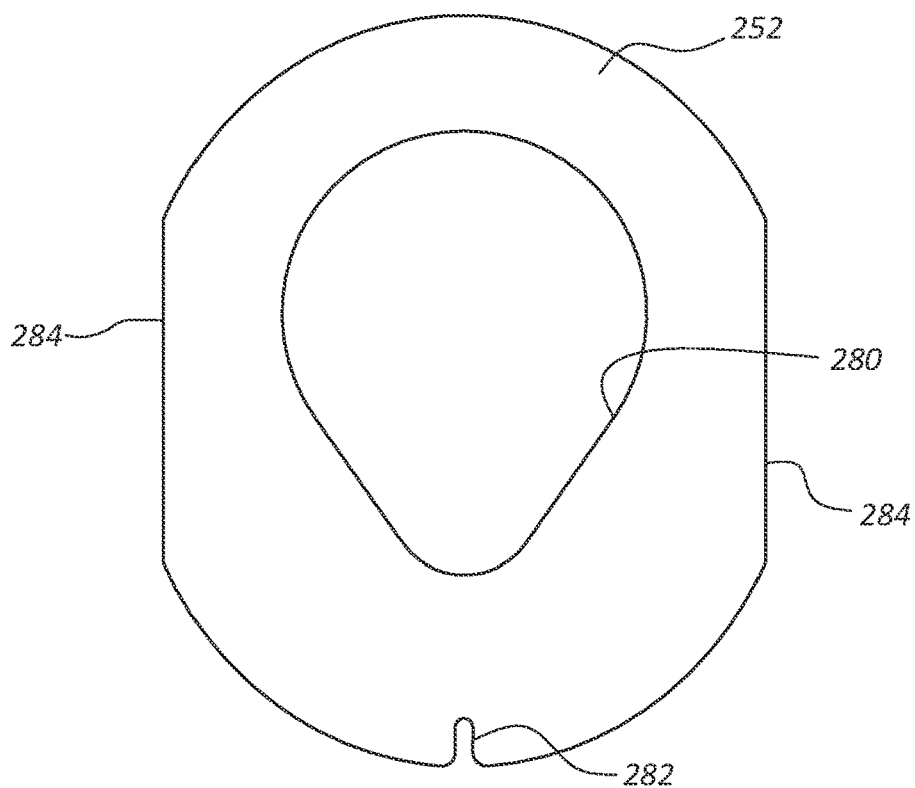

A dressing portion 252 is included to serve as a base for the dressing 210 when placed on the skin of the patient and to provide a skin-based barrier to protect the insertion site of the infusion needle or other medical device to be covered by the dressing. As seen in FIGS. 7, 9A, and 9B, the dressing 252 includes a flat, flexible body that defines a hole 280, which is aligned with, and defines a perimeter that corresponds with, both the hole 270 of the release liner 250 and the domed portion 218. A notch 282 is included and corresponds in position with the second notch 272 of the release liner 250. The dressing also defines flat sides 284, though it is appreciated that the dressing portion 252 can include any one of a variety of shapes and sizes to accommodate a variety of dressing applications.

In the present embodiment, the dressing portion 252 includes a non-woven, spunlace polyester material, though it is appreciated that various other materials can be acceptably used. For instance, a knitted polyester could be employed. Desired characteristics for the dressing material include one that can suitably carry the adhesives disposed thereon (discussed below), offers suitable tensile and general strength for retaining the infusion needle assembly and its tubing without tearing and for supporting the domed portion 218, and suitably prevents rolling of the cover film, discussed below.

The bottom surface of the dressing portion 252 includes an adhesive configured to bond the dressing portion to the skin of the patient when the dressing 210 is placed. Though various biocompatible adhesives may be used, in the present embodiment an acrylic adhesive, such as LOCTITE® 737NA acrylic adhesive, is employed for the bottom surface of the dressing portion 252. Other possible adhesives include silicone-based, urethane-based, and hydrocolloid adhesives.

Figure 10A:
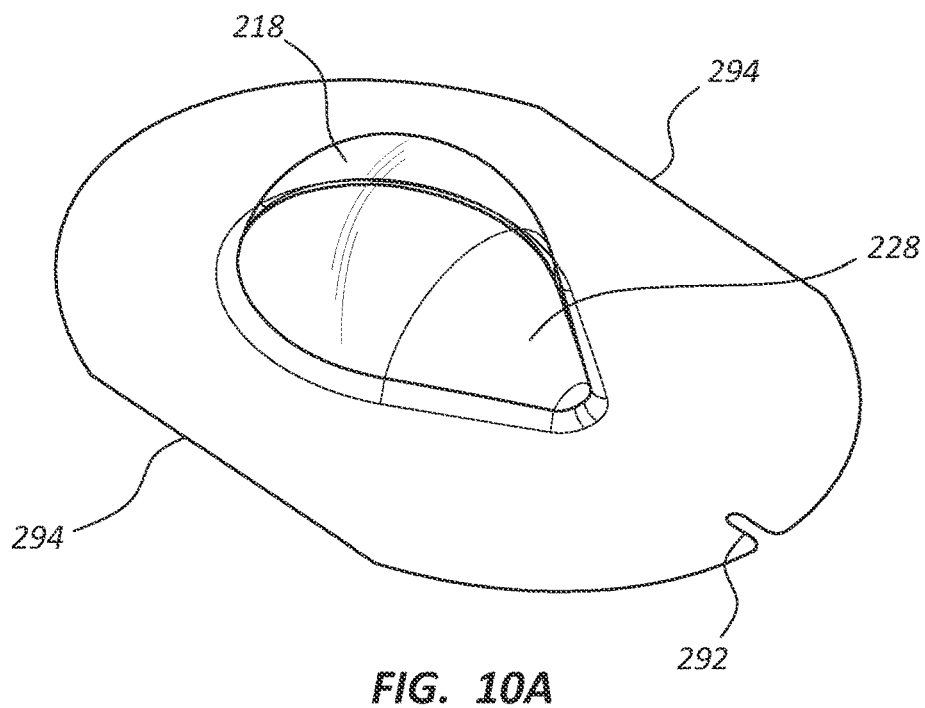
FIGS. 10A and 10B show various views of a portion of the medical device dressing of FIGS. 6A-6D.
Figure 10B:
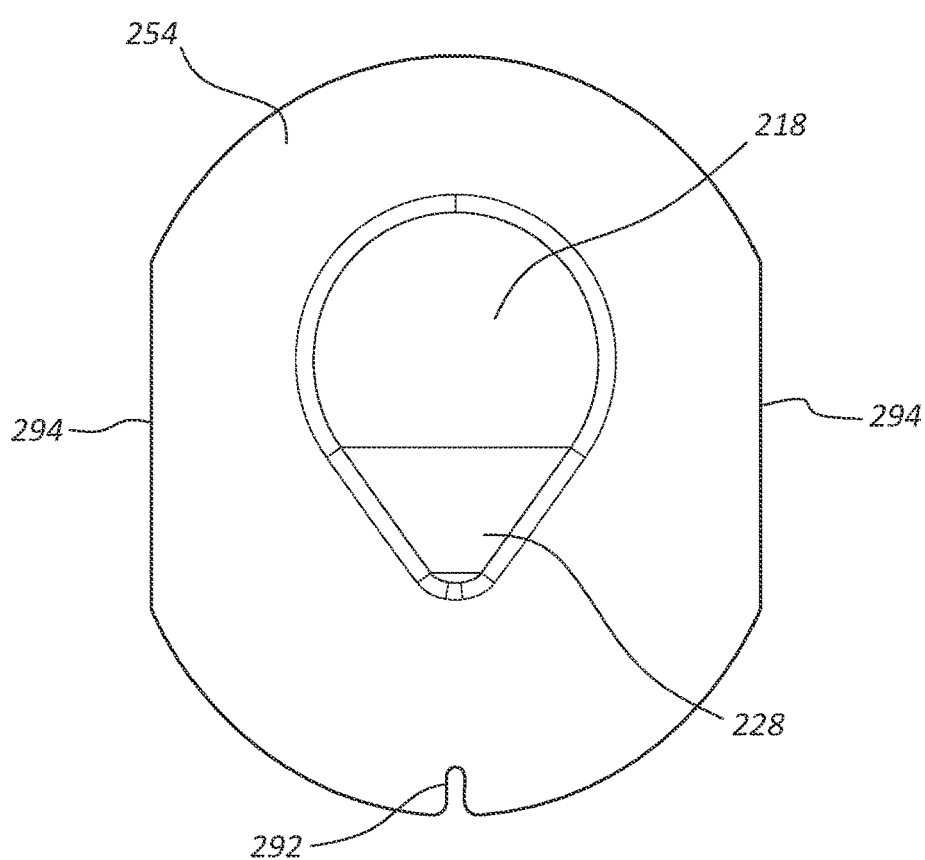

A cover film 254 is included atop the dressing portion 252 to provide a cover for the infusion needle assembly or other skin-placed medical device to be covered by the dressing 210. As seen in FIGS. 7, 10A, and 10B, the cover film 254 includes a flexible body that defines a flat perimeter about the domed portion 218, which is also defined by the cover film. The cover film 254 defines a notch 292 that corresponds in position with both the notch 282 of the dressing portion 252 and the second notch 272 of the release liner 250. The notch 292, together with the notch 282, provides an exit site for the tubing of an infusion needle assembly or other medical device covered by the dressing 210, as will be seen. Like the dressing portion 252, the cover film 254 includes flat sides 294, which correspond with the flat sides 284 of the dressing portion 252, though it is appreciated that the cover film 254 can include any one of a variety of shapes and sizes to accommodate a variety of dressing applications.

In greater detail and as has been described in connection with other embodiments, the pliable domed portion 218 and its point 228 are defined by a raised central portion of the otherwise flat cover film 254 to define the cavity 224 for protecting and isolating the skin-placed medical device, though it is appreciated that the domed portion could be located in other positions on the dressing 210 as well. The particular size, shape, and configuration of the domed portion 218 can vary from what is shown and described herein. The domed portion 218 illustrated in FIGS. 7, 10A, and 10B, for instance, is configured to cover various types of skin-placed infusion needle assemblies. The pliable nature of the domed portion 218 enables it to be collapsed during packaging and before use, then easily expanded up to define the cavity 224 when the dressing 210 is ready to be placed atop the medical device on the skin surface of the patient.

In the present embodiment, the cover film 254 includes a thermoplastic polyurethane film, such as ARGOMEDPLUS® 18411 polyurethane material available from Argotec LLC of Greenfield, Mass., though other suitable materials, including other polymeric materials, could be utilized. Desired characteristics of the material for film cover 254 in one embodiment include: suitably high resilience to deformation/elongation; sufficient vapor transmissiveness; and abrasion, puncture and tear resistance. The thickness of the thermoplastic polyurethane film to be used in manufacturing the cover film 254 is about 2.25 mils, in one embodiment, though the thickness can vary according to the material selected. In another embodiment, the thickness of the thermoplastic polyurethane film is from about 1.5 to about 2.5 mils.

The use of polyurethane as the cover film material enables the domed portion 218 to be pliable while retaining sufficient strength to form its dome shape. Further, the above-described thicknesses of the polyurethane cover film material enables the dome portion 218 to retain a desired moisture vapor transfer rate therethrough. This in turn prevents undesired moisture buildup within the cavity 224 of the domed portion 218 during use of the dressing 210 on the skin surface of the patient. The domed portion 218, together with the other portions of the dressing 210 cooperate to isolate the skin-placed medical device over which the dressing is disposed so as to prevent the incursion of microbes into the cavity 224 of the domed portion, thus preventing infection/compromise of the insertion site of the medical device through the skin of the patient.

An acrylic adhesive or other suitable adhesive is employed between the top surface of the dressing 252 and the bottom surface of the cover film 254 (from the perspective shown in FIG. 7) so as to prevent separation of the two components.

Figure 11A:
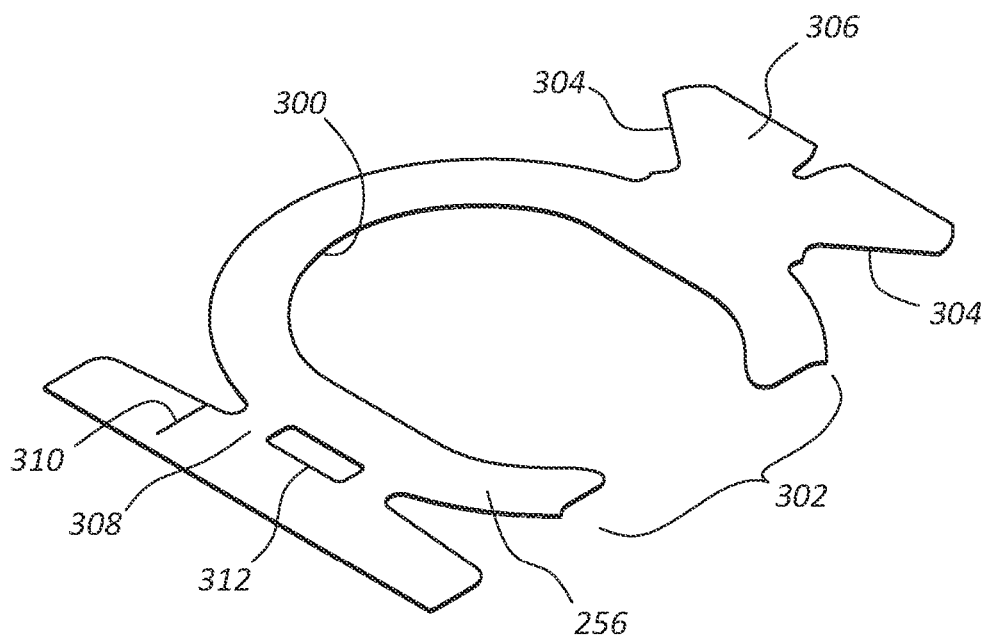
FIGS. 11A and 11B show various views of a portion of the medical device dressing of FIGS. 6A-6D.
Figure 11B:
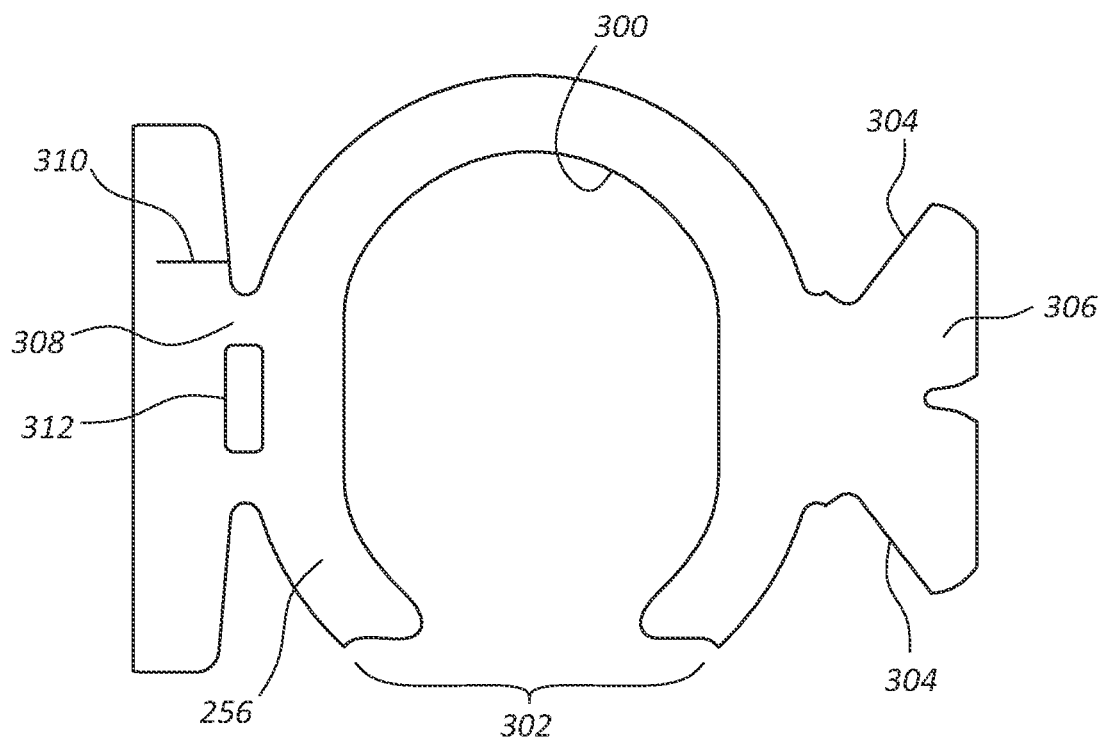

A support frame 256 is included to provide stiffness before and during placement of the dressing 210 over the skin-placed medical device and the skin of the patient. As seen in FIGS. 6, 11A, and 11B, the support frame 256 includes a flat, flexible body that includes a hole 300 such that the body generally defines a horseshoe shape. A cutout 302 is included to enable application of a securement component to the dressing 210 during dressing application. Cutouts 304 are also included on a first support portion 306 of the support frame 256 to help enable removal of a securement component, such as a tube securement assembly 260, which is mounted thereon, as will be described further below. A second support portion 308 is also included on the support frame 256 to provide a mounting surface for a tape strip 264, a date/time strip 262, and/or other component of the dressing 210, as will be seen further below.

A slit 310 is provided on the second support portion 308 to assist in removal of the afore-mentioned tape strip 264, as will be seen. Also, a hole 312 is included adjacent the date/time strip 262 to assist with removal of the date/time strip from the support frame 256, as will be seen. Similar holes can be positioned at other locations on the support frame to assist with the removal of other components removably attached to the support frame, in other embodiments. In yet another embodiment, slits in the support frame can be positioned proximate or under the date/time strip or other removable component so as to promote folding of the support frame and ease removal of the date/time strip from the support frame.

In the present embodiment, the support frame 256 includes a super-calendered kraft paper, though it is appreciated that other materials can also be employed, including polymers including polyethylene, polypropylene, polystyrene, etc. A silicone or other suitable coating is added to the top surface of the support frame 256 in the present embodiment to enable ease of removal of the tube securement assembly 260, date/time strip 262, and the tape strip 264 from the support frame. In the present embodiment, a suitable adhesive, such as a hot-melt adhesive, is applied to permit the attachment of the support frame to the cover film 254 and to permit separation thereof when desired. In one embodiment, the support frame material is pre-attached to the cover film material prior to assembly of the dressing 210. Other suitable support frame adhesives may also be employed.

Figure 12A:
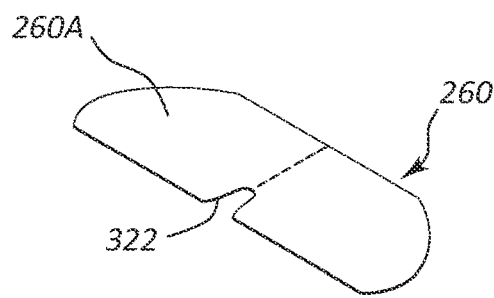
FIGS. 12A and 12B show various views of a portion of the medical device dressing of FIGS. 6A-6D.
Figure 12B:
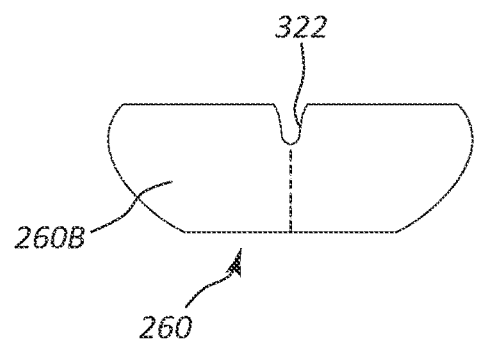

FIGS. 7, 12A, and 12B show that the tube securement assembly 260 includes a body including a dressing portion 260A and a cover film portion 260B that are adhesively or otherwise joined to one another. In the present embodiment, the dressing portion 260A includes a non-woven, spunlace polyester material similar to that of the dressing portion 252, while the cover film portion 260B includes thermoplastic polyurethane film, such as ARGOMEDPLUS® 18411 polyurethane material, similar to that of the cover film 254. Of course, other suitable materials can be employed. Though various biocompatible adhesives may be used, in the present embodiment an acrylic adhesive, such as LOCTITE® 737NA acrylic adhesive, is included on the bottom surface of the dressing portion 260A of the tube securement assembly 260 to enable it to be applied to the dressing 210 and the skin of the patient, as will be discussed.

Figure 13A:
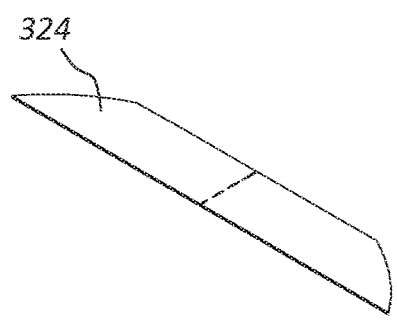
FIGS. 13A and 13B show various views of a portion of the medical device dressing of FIGS. 6A-6D.
Figure 13B:
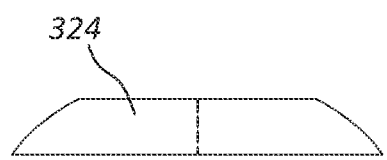

A notch 322 is defined in the body of the tube securement assembly 260 and corresponds in position with a corresponding notch on the support frame 256 and the notch 271 on the release liner 250. FIGS. 13A, 13B show that a removable support frame portion 324, including a kraft paper or other suitably stiff material, is applied to a portion of the top surface of the body of the tube securement assembly 260 to provide increased rigidity during placement of the tube securement assembly, discussed below.

The tube securement assembly 260 is removably applied to the top surface of the support frame 256 on the first support portion 306 thereof, as shown in FIG. 6B. Note that the size, shape, and placement of the tube securement assembly can vary from what is shown and described herein.

Figure 14A:
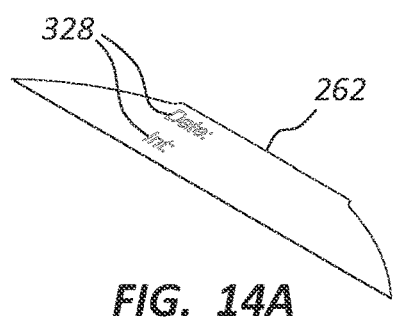
FIGS. 14A and 14B show various views of a portion of the medical device dressing of FIGS. 6A-6D.
Figure 14B:
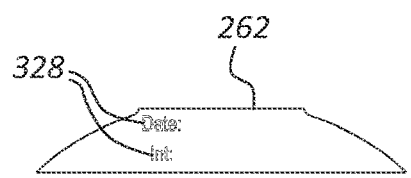

FIGS. 14A and 14B show that the date/time strip 262—including a non-woven polyester, gauze, fabric, or other suitable material—is removably disposed on the top surface of the support frame 256 on the second support portion 308 thereof, as shown in FIG. 6B. A date/time insignia 328, or other insignia, is disposed on the top surface of the date/time strip 262 to enable data regarding placement of the medical device and/or dressing 210 to be recorded.

Figure 15A:
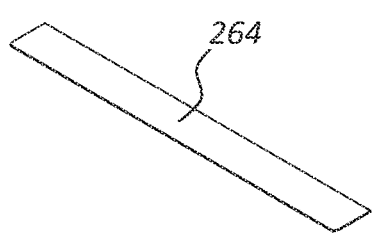
FIGS. 15A and 15B show various views of a portion of the medical device dressing of FIGS. 6A-6D.
Figure 15B:
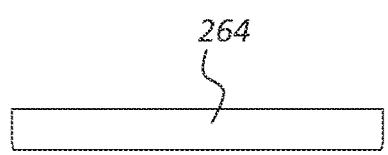

FIGS. 15A and 15B show that the elongate adhesive tape strip 264 is removably disposed on the top surface of the support frame 256 on the second support portion 308 thereof, proximate the date/time strip 262, as shown in FIG. 6B. The tape strip 264 can be used to further secure the skin-placed medical device by applying the tape strip over the domed portion 218, to further securing the tubing of the medical device by applying the tape strip over the tube securement assembly 260, to secure the medical device to the skin before placement of the dressing, or to assist in other ways with placement of the dressing 210 on the skin of the patient. Note that the slit 310 included on the support frame 256 (FIGS. 11A, 11B) assists in removing the tape strip 264 from the support frame. In brief, the relatively small portion of the support frame 256 above the slit 310 is ripped off with the tape strip 264 when the tape strip is removed from the support frame, which provides a non-adhesive location on the tape strip to enable the clinician to easily handle the tape strip. Once the tape strip 264 has been placed, the ripped-off portion of the support frame 256 can be removed from the back of the tape strip, and discarded.

FIG. 16 shows that the release liner 250 in the present embodiment includes two extended surfaces, or underhang portions 340, on either end of the dressing 210, which assist the user in grasping and removing the release liner from the rest of the dressing 210 during placement on the skin of the patient. Also shown in FIG. 16 are the two cutouts 304 for assisting the user in grasping and removing the tube securement assembly 260 from the support frame 256. The cutouts 304 are located in an interior position of the dressing 210 as opposed to being located on an outer edge of the dressing, which enables the user to more easily remove the tube securement assembly 260 from the support frame 256 with one hand. Thus, together with the right overhang 340 shown in FIG. 16, the cutouts 304 provide three access points for the user to peel away the tube securement assembly 260 from the support frame 256. Such cutouts can be employed in other areas of the dressing, in other embodiments.

Reference is now made to FIGS. 17A-17D in describing details relating to the placement of the dressing 210 on the skin of the patient over a skin-placed medical device, according to the present embodiment. Note that the dressing 210 in one embodiment is first removed from a sterilized package using suitable sterilization techniques. The release liner 250 is peeled off the back of the dressing 210, using the extended underhang portions 340 (FIG. 16) to help grab the release liner.

Figure 17A:
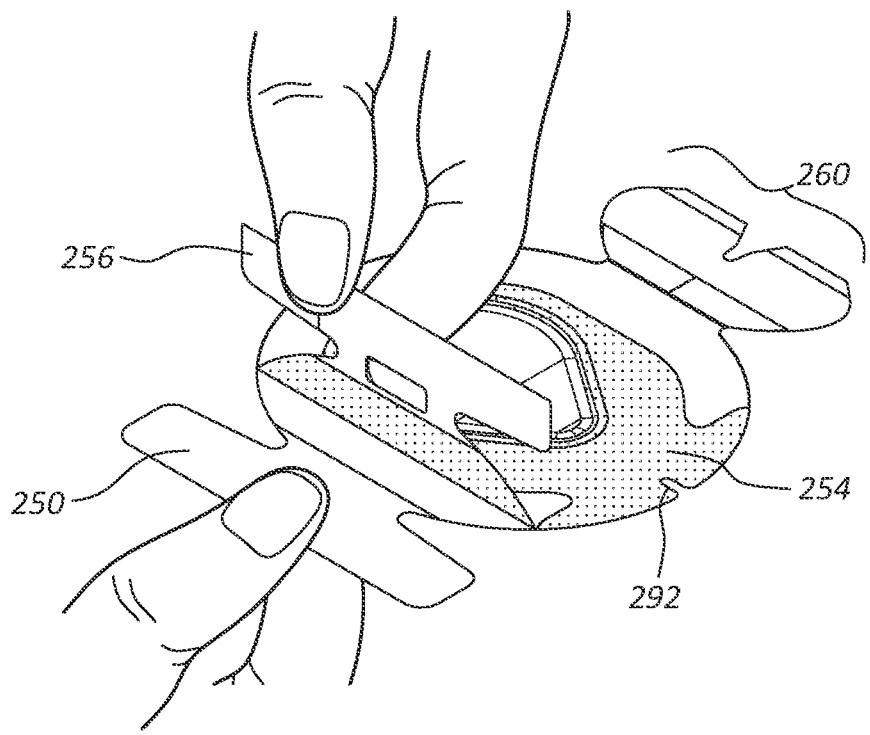
FIGS. 17A-17D show various views depicting placement of the medical device dressing of FIGS. 6A-6D on a skin surface of a patient.
Figure 17B:
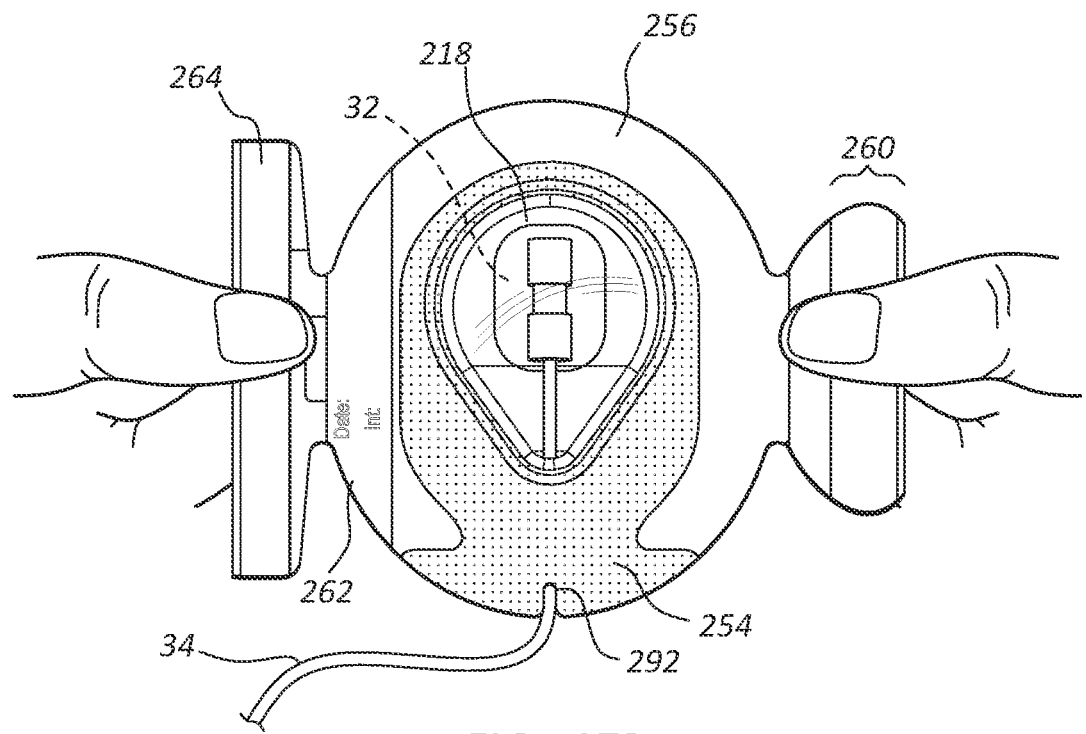

Once the release liner 250 has been removed, the dressing 210 is placed over a medical device disposed on the skin of the patient, such as the infusion needle assembly 32 shown in FIG. 17B. The dressing 210 is pressed down so as to be affixed to the skin surface of the patient, taking care to orient the dressing such that the infusion needle assembly 32 is received within the cavity 224 of the teardrop-shaped domed portion 218 and the point 228 of the domed portion is substantially aligned with tubing 34 of the infusion needle assembly and the tubing extends through the notch 282, 292 of the joined dressing portion 252 and cover film 254. The dressing 210 is pressed downward so that the adhesive on the bottom surface of the dressing portion 252 adheres to the skin and around the tubing extending under the dressing portion, noting that no adhesive is present on the domed portion 218. The dressing 210 is secured such that the infusion needle assembly 32 is isolated within the dressing, thus protecting it from contamination, incursion of microbes, etc. In one embodiment, the domed portion of the dressing engages a top portion of the infusion needle assembly or other medical device so as to help maintain the medical device in position on the skin of the patient.

Figure 17C:
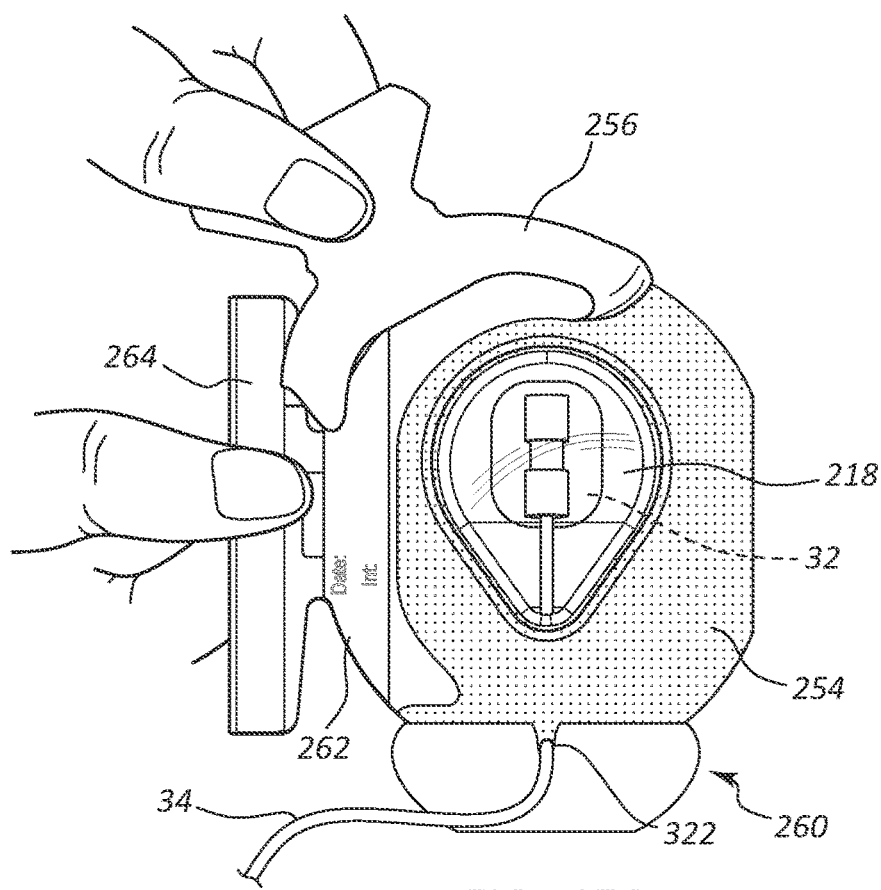

The tube securement assembly 260 is then removed from atop the support frame 256 and placed over the portion of the tubing 34 that extends from the notches 282, 292 so as to overlap both the skin of the patient and the adjacent portion of the dressing 210 and such that the notch 322 receives a portion of the tubing therein, as seen in FIG. 17C. The support frame portion 324 provided added rigidity to help handle and place the tube securement assembly 260 in its desired position. After placement, the support frame portion 324 can be peeled away from the tube securement assembly 260 and discarded. In this way, the tubing 34 is further secured against unintended displacement and is further isolated so as to prevent migration of impurities into the cavity 224 of the domed portion 218 and the infusion needle assembly 32 disposed therein. Further, placement of the tube securement assembly 260 in this manner prevents the tubing 34 from lifting up the edge of the dressing 210 (and thus compromising the isolation of the infusion needle assembly 32) should a pulling force be applied to the tubing. Note that the cutout 302 of the support frame 256 enables the tube securement assembly to be placed on the dressing 210 without first having to remove the support frame.

It is appreciated that in one embodiment the tube securement assembly is integrally formed with the dressing body; in another embodiment, no tube securement assembly is included. The size, shape, configuration, and placement of the tube securement assembly can also vary from what is shown and described herein. In another embodiment the securement assembly is used to secure components other than tubing. For instance, the securement assembly can be used to secure the dressing itself, in one embodiment.

Figure 17D:
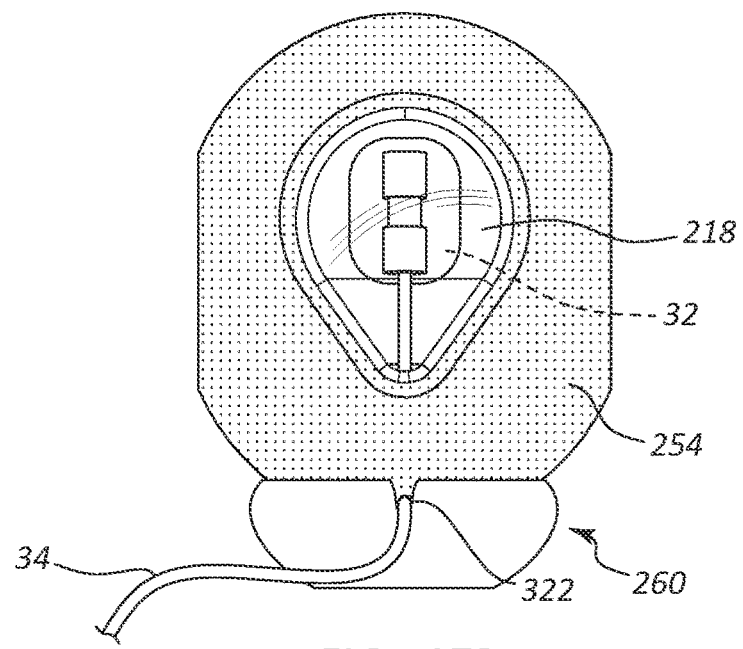

Once the tube securement assembly 260 has been positioned, the support frame can then be removed from the dressing 210, as shown in FIG. 17C, resulting in the dressing placement shown in FIG. 17D. If desired, the date/time strip 262 can be peeled away from the recently-removed support frame 256, using the hole 312 that allows a finger of the user to grasp the bottom surface of the date/time strip. The date/time strip 262 can then be placed on the cover film 254 of the dressing 210, the tube securement assembly 260, or in another suitable location. Also if needed, the tape strip 264 can be removed from the support frame 256 and utilized on the dressing 210, as already described further above.

It is appreciated that, in one embodiment, no support frame is included in the dressing. In such a case, the release liner can optionally be made relatively thicker to provide for the desired stiffness of the dressing.

The dressing 210 is manufactured in one embodiment by first joining the dressing portion 252 to cover film 254. In particular, an adhesive (described further above) is applied to the top surface of the dressing portion 252 and the cover film 254, with the support frame 256 pre-attached thereto, is attached to the dressing portion. At this stage, the domed portion 218 has not yet been defined in the cover film 254.

The dressing portion 252 and joined cover film 254 can be pre-cut to define the respective sides 284, 294, or be cut after being joined together. The release liner 250 can then be joined to the bottom surface of the dressing portion 252. The holes 270, 280 of the respective release liner 250 and dressing portion 252 can be pre-defined or defined after joining of the release liner and the dressing portion. Excess material about the support frame 256 can be removed at this time, in the present embodiment.

The pre-assembled tube securement assembly 260 can be attached to the top surface of the support frame 256, as can the date/time strip 262 and the tape strip 264. Note that, in one embodiment, the final shapes of the tube securement assembly 260, the date/time strip 262, and the tape strip 264 can be defined at this stage via a die cut procedure. In another embodiment, the final shapes of these components can be pre-defined prior to attachment to the support frame 256.

Next, the assembled dressing 210 is electrostatically neutralized via an ionizer to eliminate static electricity before being introduced to a thermal forming process, wherein the dressing is positioned such that the holes 270 and 280 of the release liner 250 and the dressing portion 252 are aligned with a negative-type mold. A vacuum is applied and heat is introduced to the dressing so that the central portion of the cover film 254 is sucked on to and thermally formed about the mold, thus defining the pliable domed portion 218 in the cover film 254. In one embodiment, holes are included in the mold to assist in sucking the cover film on to the mold surface. Note that the release liner 250 acts as a heat shield to protect the dressing portion 252 and the cover film 254 from heat damage during the thermal forming process, in one embodiment. The heat and vacuum are then removed and the dressing 210 is allowed to cool, which causes the domed portion 218 to be permanently defined.

Figure 5:
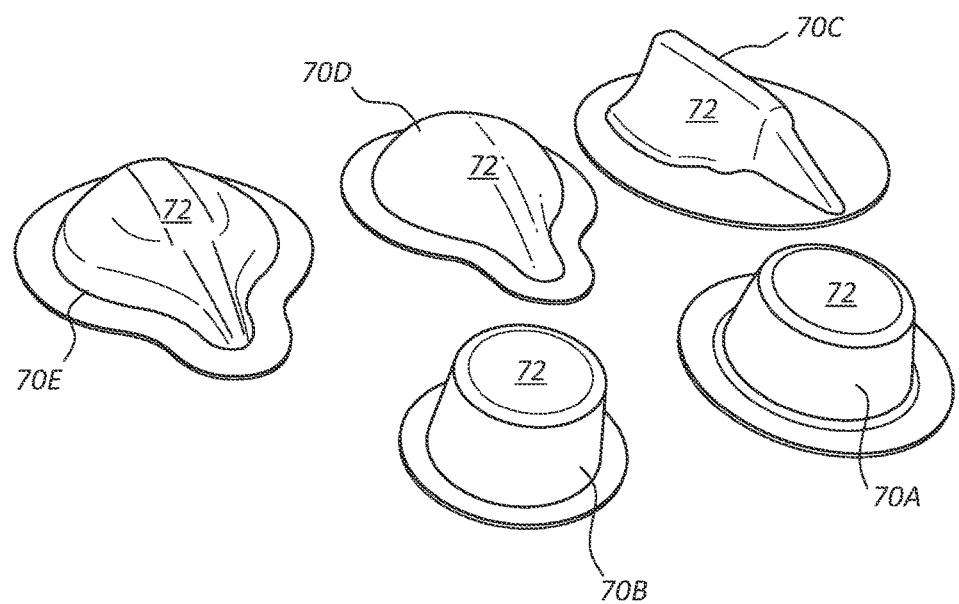
FIG. 5 shows various views of a plurality of molds used in forming a medical device dressing according to one embodiment.

Note that the mold can be a negative or positive form of the desired shape for the domed portion 218. Indeed, FIG. 5 shows various examples of positive molds 70A-70E, each including a shaped body 72. Note also that the shapes of the molds can vary from what is shown and described herein. In one embodiment, a positive air pressure could be employed to force the cover film on to the mold surface.

When forming the domed portion in the above-described manner utilizing a polyurethane cover film 254 of about 2 mils thickness as detailed further above, the thickness of the resultant domed portion 218 is from about 0.65 mil to about 1 mil, in one embodiment.

In other embodiments, other modes for forming the domed portion can be employed, including cold forming (rolling), injection molding, utilizing a pre-formed cover film, and dip casting, in which a form is repeatedly dipped into a molten polyurethane (or other suitable material) and solvent mixture to build up a domed portion cover film. These and other forming techniques are therefore contemplated. It is also appreciated that the above-described manufacturing steps are not exhaustive and that a different order of steps could be employed.

Figure 18A:
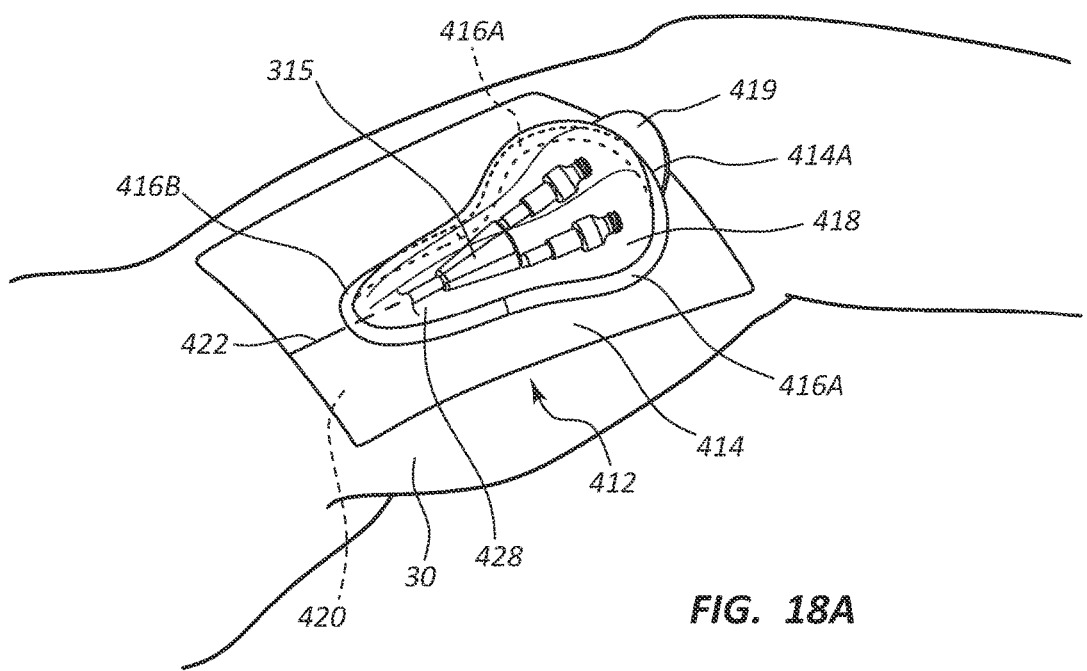
FIGS. 18A and 18B are various views of a medical device dressing according to one embodiment.
Figure 18B:
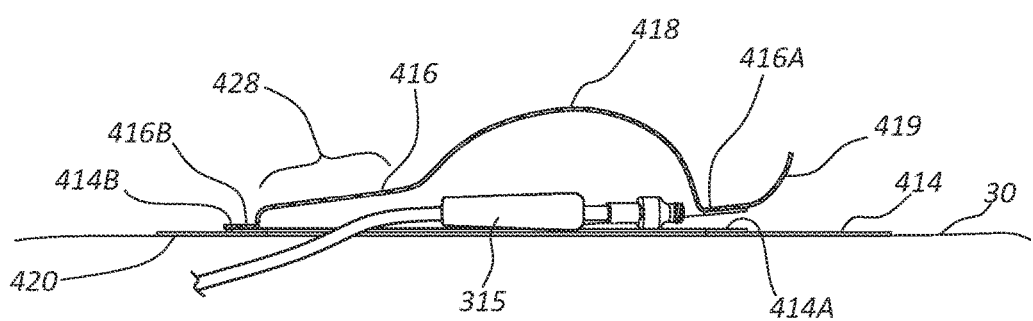

FIGS. 18A and 18B depict a dressing 410 according to one embodiment, including a body 412 defined by a flexible, flat perimeter portion 414 that surrounds a central portion 416 as in previous embodiments. The central portion 416 includes a pliable domed portion 418 of polyurethane or other suitable material.

A releasable portion 416A included about a proximal perimeter of the central portion 416 is configured to be resealable so that access can be selectively made to the PICC 315 or other medical device enclosed within the domed portion 418. A pull-tab 419 or the like is included to facilitate lifting of the proximal portion of the central portion 416. When closed, the releasable portion 416A adheres to a releasable adhesive included on the perimeter portion 414 directly below the releasable portion, indicated in FIGS. 15A and 15B as a release layer portion 414A, so as to maintain isolation of the domed portion 418 when closed.

Correspondingly, an adhered portion 416B is included about a distal perimeter of the central portion 416 and is configured to not separate from attachment with the perimeter portion 414. The adhesive used to secure the adhered portion 416B to the perimeter portion 414 can be the same adhesive as an adhesive 420 that is employed to secure the other portions of the central portion 416 to the perimeter portion 414. The relative sizes, shapes, and extents of both the releasable portion 416A and the adhered portion 416B can be varied from what is shown and described herein. A slit 422 can be included in the perimeter portion 414 to enable removal of the dressing 410 from over the medical device. As in other embodiments, the domed portion 418 can include a notch, or point 428, to fit over a portion of the covered medical device.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A dressing for covering a medical device on a skin surface of a patient, comprising:
   a dressing portion configured to rest against the skin surface of the patient, the dressing portion defining a hole;
   a polymeric cover film permanently attached to the dressing portion, the polymeric cover film including a pliable domed portion aligned with the hole of the dressing portion, the pliable domed portion defining a cavity configured to receive therein the medical device when the dressing is placed on the skin surface of the patient; and
   a support frame removably attached to the polymeric cover film to provide rigidity during placement of the dressing on the patient, the support frame including a cutout portion enabling a securement component to be attached to the cover film without removal of the support frame, the securement component removably disposed on a top surface of the support frame before use.

2. The dressing as defined in claim 1, wherein the domed portion is collapsible to enable placement of the dressing in a substantially flat package.

3. The dressing as defined in claim 2, wherein the dome portion is formed via a thermal forming process using a mold.

4. The dressing as defined in claim 3, wherein heat from the thermal forming process is directed through the hole defined in the dressing so as to impinge on the cover film.

5. The dressing as defined in claim 4, wherein the dressing portion includes non-woven polyester and wherein the cover film includes a thermoplastic polyurethane.

6. The dressing as defined in claim 5, further comprising a release liner removably attached to a bottom surface of the dressing portion, the release liner defining a hole aligned with the hole of the dressing portion.

7. The dressing as defined in claim 6, wherein the release liner provides heat shielding for the dressing portion and the cover film during the thermal forming process, and wherein the dome portion prevents tenting of the dressing when the dressing is placed over the medical device on the skin surface of the patient.

8. The dressing as defined in claim 1, wherein the securement component includes a tube securement assembly for securing tubing of the medical device covered by the dressing.

9. The dressing as defined in claim 1, wherein the domed portion is substantially teardrop-shaped.

10. The dressing as defined in claim 1, wherein the cover film includes a thickness proximate an outer perimeter thereof of 2.25 mils, and wherein the domed portion includes a thickness of from 0.65 mil to 1 mil.

11. The dressing as defined in claim 1, wherein the medical device includes an infusion needle assembly.

12. The dressing as defined in claim 11, wherein the cover film and the dressing portion include aligned notches to enable tubing of the medical device to exit the dressing, and wherein a securement component including a notch is placed over the tubing in alignment with the notches of the cover film and the dressing portion.

13. A method of manufacturing a dressing for covering a medical device on a skin surface, the method comprising:
providing a dressing portion defining a hole;
attaching a polymeric cover film to the dressing portion;
forming a pliable domed portion in the polymeric cover film after the polymeric cover film is attached to the dressing portion to align a perimeter of the domed portion with the hole defined in the dressing portion;
removably attaching a release liner to a bottom surface of the dressing portion;
removably attaching a support frame to a top surface of the polymeric cover film;
removably attaching a tube securement assembly to a support portion of the support frame, the support portion including at least one cutout portion to enable a user to easily remove the tube securement assembly from the support frame, the at least one cutout portion disposed inward from an outer perimeter of the support frame.

14. The method of manufacturing as defined in claim 13, wherein attaching the cover film includes attaching the cover film to the dressing portion using an acrylic adhesive.

15. The method of manufacturing as defined in claim 13, wherein forming the pliable domed portion includes thermally forming the pliable domed portion.

16. The method of manufacturing as defined in claim 15, wherein thermally forming the pliable domed portion further comprises:
applying a vacuum to force a portion of the cover film into proximity with a mold; and
applying heat to the cover film while the portion of the cover film is in proximity with the mold such that the domed portion is formed.

17. A dressing for covering a medical device on a skin surface of a patient, comprising:
a release layer;
a dressing portion removably attached to the release layer, the dressing portion configured to rest against the skin surface of the patient, the dressing portion defining a hole having an outer perimeter;
a polymeric cover film attached to the dressing portion, the polymeric cover film including a pliable domed portion having a shape corresponding to the outer perimeter of the hole of the dressing portion, the pliable domed portion defining a cavity configured to receive therein the medical device when the dressing is placed on the skin surface of the patient;
a support frame removably attached to the polymeric cover film configured to provide rigidity to the dressing; and
a securement component removably attached to the support frame, the securement component configured to secure a portion of the medical device, wherein the support frame includes a gap configured to enable the securement component to be removed from the support frame and attached to the polymeric cover film without removing the support frame from the polymeric cover film.

18. The dressing as defined in claim 17, further comprising a tape strip that is removably attached to the support frame.

19. The dressing as defined in claim 18, wherein a slit is included on the support frame beneath the tape strip to enable the tape strip to be readily removed from the support frame.

20. The dressing as defined in claim 17, further comprising a date/time strip that is removably attached to the support frame.

21. The dressing as defined in claim 20, wherein a hole is defined by the support frame proximate the date/time strip to enable the date/time strip to be manually grasped by a user.

22. The dressing as defined in claim 17, wherein the domed portion includes a predetermined moisture vapor transfer rate to enable moisture to escape from the domed portion.

23. The dressing as defined in claim 17, wherein the securement component comprises a tube securement assembly including a dressing portion, a cover film portion, and a removable support frame portion, the tube securement assembly configured to secure tubing of the medical device at an exit point from the dressing.

24. The dressing as defined in claim 17, wherein the polymeric cover film includes a thermoplastic polyurethane including a thickness of from 1.5 mils to 2.5 mils.

25. The dressing as defined in claim 17, wherein the domed portion is transparent and wherein the domed portion includes at least one reinforcement feature configured to provide strength to the domed portion.

* * * * *